United States Patent
Yamakabe et al.

(10) Patent No.: US 12,236,714 B2
(45) Date of Patent: Feb. 25, 2025

(54) INFORMATION PROCESSING SYSTEM, INFORMATION PROCESSING APPARATUS, INFORMATION PROCESSING METHOD, AND RECORDING MEDIUM

(71) Applicant: NEC Corporation, Tokyo (JP)

(72) Inventors: Ryo Yamakabe, Tokyo (JP); Ryuichi Akashi, Tokyo (JP); Yuka Ogino, Tokyo (JP); Kosuke Yoshimi, Tokyo (JP); Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/776,314

(22) PCT Filed: Sep. 14, 2021

(86) PCT No.: PCT/JP2021/033693
§ 371 (c)(1),
(2) Date: May 12, 2022

(87) PCT Pub. No.: WO2023/042248
PCT Pub. Date: Mar. 23, 2023

(65) Prior Publication Data
US 2024/0153310 A1 May 9, 2024

(51) Int. Cl.
*G06V 40/18* (2022.01)
*G06V 10/25* (2022.01)
(Continued)

(52) U.S. Cl.
CPC ............ *G06V 40/193* (2022.01); *G06V 10/25* (2022.01); *G06V 10/761* (2022.01); *H04N 23/67* (2023.01)

(58) Field of Classification Search
None
See application file for complete search history.

(56) References Cited

U.S. PATENT DOCUMENTS

2002/0080259 A1 6/2002 Izumi
2012/0248190 A1 10/2012 Ogawa et al.
(Continued)

FOREIGN PATENT DOCUMENTS

CN 112394507 A 2/2021
JP H10-229516 A 8/1998
(Continued)

OTHER PUBLICATIONS

International Search Report for PCT Application No. PCT/JP2021/033693, mailed on Nov. 22, 2021.
(Continued)

*Primary Examiner* — Delomia L Gilliard

(57) ABSTRACT

An information processing system (10) comprises: a distance acquisition unit (110) that specifies an iris area containing an iris of a target from a visible-light image of the target, and acquires an iris distance that is a distance to the iris area; an iris image acquisition unit (120) that acquires an iris image of the target by changing a focal length according to the iris distance; a score computing unit (130) that calculates a score relating to deviation of a focus in the iris image, based on the iris image; and a correlation update unit (140) that updates correlation between the iris distance and the focal length at a moment of acquisition of the iris image, based on the score. According to such an information processing system, since the correlation is updated with good accuracy, it is possible to acquire the appropriate iris image.

6 Claims, 17 Drawing Sheets

(51) Int. Cl.
  *G06V 10/74* (2022.01)
  *H04N 23/67* (2023.01)

(56) References Cited

U.S. PATENT DOCUMENTS

| | | |
|---|---|---|
| 2020/0096678 A1 | 3/2020 | Kaminski et al. |
| 2023/0083281 A1* | 3/2023 | Oami ..................... G06T 1/00 726/22 |
| 2023/0100016 A1 | 3/2023 | Yamakabe et al. |

FOREIGN PATENT DOCUMENTS

| | | | |
|---|---|---|---|
| JP | 2001-358987 A | | 12/2001 |
| JP | 2002085382 A | * | 3/2002 |
| JP | 2002-122778 A | | 4/2002 |
| JP | 2004226729 A | * | 8/2004 |
| JP | 2012154825 A | * | 8/2012 |
| JP | 2012-208797 A | | 10/2012 |
| JP | 2020-516936 A | | 6/2020 |
| WO | 2015/001634 A1 | | 1/2015 |
| WO | 2020/261368 A1 | | 12/2020 |
| WO | WO-2021166223 A1 * | 8/2021 | ............. G06F 21/32 |
| WO | 2021/171586 A1 | | 9/2021 |

OTHER PUBLICATIONS

Extended European Search Report for EP Application No. 21957432.4, dated on Sep. 13, 2024.

\* cited by examiner

FIG.14

CORRELATION
NOW UPDATING···

PLEASE DO NOT MOVE

INFORMATION PROCESSING SYSTEM, INFORMATION PROCESSING APPARATUS, INFORMATION PROCESSING METHOD, AND RECORDING MEDIUM

This application is a National Stage Entry of PCT/JP2021/033693 filed on Sep. 14, 2021, the contents of all of which are incorporated herein by reference, in their entirety.

TECHNICAL FIELD

The disclosure relates to technical fields of an information processing system, an information processing apparatus, an information processing method, and a recording medium.

PRIOR ART

There is known as this type of system, a system that automatically adjusts the focal length of a camera. For example, disclosed in Patent Document 1 is a technique for changing, by measuring the distance from the subject using an external light AF sensor, the focal position of an electronic still camera based on the measurement result. Disclosed in Patent Document 2 is a technique of moving the position of the focus lens group based on the measurement result of a subject distance. Disclosed in Patent Document 3 is a technique of storing a correlation between the focal length and the applied voltage of the liquid lens to adjust the focus. Disclosed in Patent Document 4, a technique of correcting voltage applied to a variable focus lens. Disclosed in Patent Document 5, a technique for storing the relationship between the distance and the applied voltage with respect to the liquid lens as a table. Disclosed in Patent Document 6 is a technique that imaging is performed while gradually changing the focal position in an iris camera.

CITATION LIST

Patent Document

Patent Document 1: JP-10-229516 A
Patent Document 2: JP 2002-122778 A
Patent Document 3: JP 2012-208797 A
Patent Document 4: WO 2015/001634 A1
Patent Document 5: JP 2020-516936 A
Patent Document 6: WO 2020/261368 A1

SUMMARY

Technical Problem

This disclosure aims to improve the techniques disclosed in the prior art.

Solution to Problem

One aspect of the disclosure information processing system comprises: a distance acquisition unit that specifies an iris area containing an iris of a target from a visible-light image of the target, and acquires an iris distance that is a distance to the iris area; an iris image acquisition unit that acquires an iris image of the target by changing a focal length according to the iris distance; a score computing unit that calculates a score relating to deviation of a focus in the iris image, based on the iris image; and a correlation update unit that updates correlation between the iris distance and the focal length at a moment of acquisition of the iris image, based on the score.

One aspect of the disclosure information processing apparatus comprises: a distance acquisition unit that specifies an iris area containing an iris of a target from a visible-light image of the target, and acquires an iris distance that is a distance to the iris area; an iris image acquisition unit that acquires an iris image of the target by changing a focal length according to the iris distance; a score computing unit that calculates a score relating to deviation of a focus in the iris image, based on the iris image; and a correlation update unit that updates correlation between the iris distance and the focal length at a moment of acquisition of the iris image, based on the score.

One aspect of the disclosure information processing method to be implemented by at least one computer, comprises: specifying an iris area containing an iris of a target from a visible-light image of the target, and acquiring an iris distance that is a distance to the iris area; acquiring an iris image of the target by changing a focal length according to the iris distance; calculating a score relating to deviation of a focus in the iris image, based on the iris image; and updating correlation between the iris distance and the focal length at a moment of acquisition of the iris image, based on the score.

One aspect of recording medium storing a computer program allows at least one computer to implement an information processing method, the information processing method comprising: specifying an iris area containing an iris of a target from a visible-light image of the target, and acquiring an iris distance that is a distance to the iris area; acquiring an iris image of the target by changing a focal length according to the iris distance; calculating a score relating to deviation of a focus in the iris image, based on the iris image; and updating correlation between the iris distance and the focal length at a moment of acquisition of the iris image, based on the score.

BRIEF DESCRIPTION OF DRAWINGS

FIG. 14 is a plan view showing a display example of at a moment of updating correlation by an information system according to the sixth example embodiment.

DESCRIPTION OF EXAMPLE EMBODIMENTS

Hereinafter, an example embodiment of an information processing system, an information processing apparatus, an information processing method, and a recording medium will be described with reference to the drawings.

First Example Embodiment

The information processing system according to a first example embodiment will be described with reference to FIGS. 1 to 3.
(Hardware Configuration)

First, a hardware configuration of an information processing system according to the first example embodiment will be described with reference to FIG. 1. FIG. 1 is a block diagram showing the hardware configuration of the information processing system according to the first example embodiment.

Figure 1:
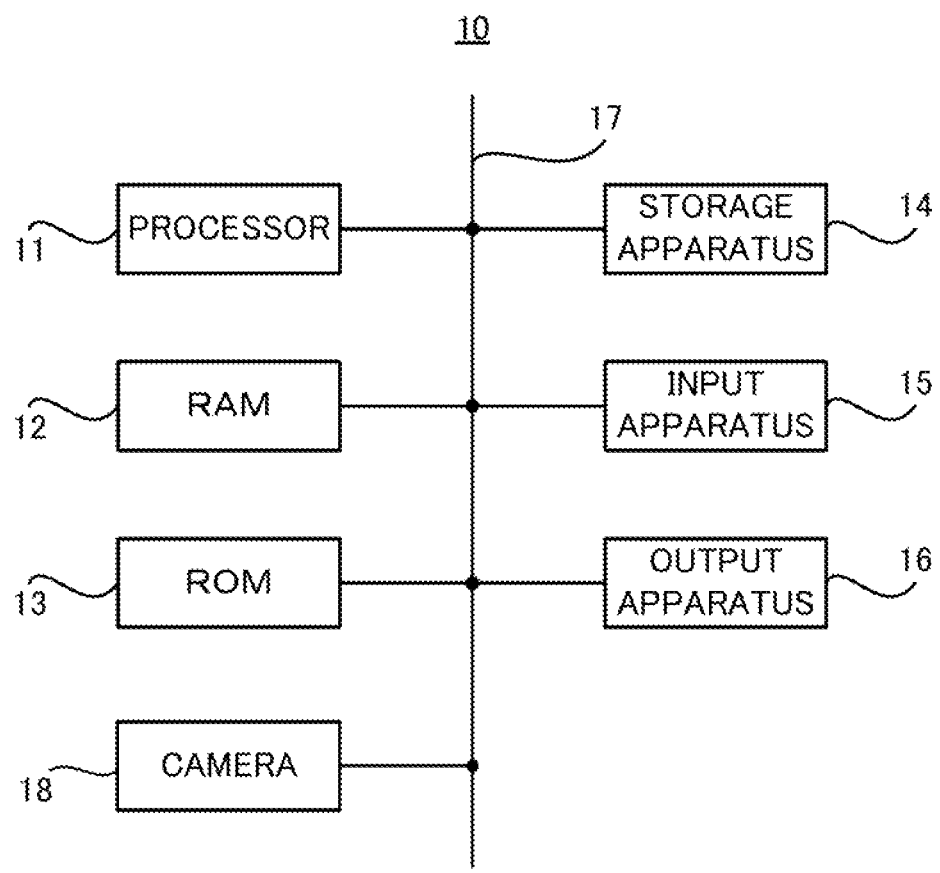
FIG. 1 is a block diagram showing a hardware configuration of an information processing system according to the first example embodiment.

As shown in FIG. 1, the information processing system 10 according to the first example embodiment comprises a processor 11, a RAM (Random Access Memory) 12, a ROM (Read Only Memory) 13, and a storage apparatus 14. The information processing system 10 may further comprise an input apparatus 15 and an output apparatus 16. The information processing system 10 may also comprise a camera 18. The processor 11 described above, the RAM12, the ROM13, the storage apparatus 14, the input apparatus 15, the output apparatus 16, and the camera 18 are connected with each other via a data bus 17.

The Processor 11 reads a computer program. For example, the processor 11 is configured to read a computer program stored in at least one of the RAM12, the ROM13 and the storage apparatus 14. Alternatively, the processor 11 may read a computer program stored in a computer readable recording medium using a recording medium reading apparatus (not illustrated). The processor 11 may acquire (i.e., read) a computer program from an apparatus (not illustrated) located external to the information processing system 10 via a network interface. The processor 11 controls the RAM12, the storage apparatus 14, the input apparatus 15, and the output apparatus 16 by implementing the computer program read. In particular, in the present example embodiment, when the computer program read by the processor 11 is implemented, realized in the processor 11 are functional blocks for updating a correlation between an iris distance and a control voltage.

The processor 11 may be configured as, for example, a CPU (Central Processing Unit), a GPU (Graphics Processing Unit), FPGA(field-programmable gate array), a DSP (Demand-Side Platform), and a ASIC(Application Specific Integrated Circuit. The processor 11 may be configured as one of these, or may be configured to use two or more of them in parallel.

The RAM12 temporarily stores the computer program which the processor 11 implements. The RAM12 temporarily stores data which the processor 11 temporarily uses when being implementing a computer program. The RAM12 may be, for example, a D-RAM(Dynamic RAM).

The ROM13 stores the computer program to be implemented by the processor 11. The ROM13 may further store fixed data. The ROM13 may be, for example, a P-ROM (Programmable ROM).

The storage apparatus 14 stores data that the information processing system 10 should preserve over a long period of time. The storage apparatus 14 may operate as a temporary storage apparatus of the processor 11. The storage apparatus 14 may include, for example, at least one of a hard disk apparatus, a magnet-optical disk apparatus, an SSD (Solid State Drive), and a disk array apparatus.

The input apparatus 15 is an apparatus that receives input instructions from a user of the information processing system 10. The input apparatus 15 may include, for example, at least one of a keyboard, a mouse, and a touch panel. The input apparatus 15 may be configured as a portable terminal, such as a smartphone or tablet.

The output apparatus 16 is an apparatus that outputs information relating to the information processing system 10 to the outside. For example, the output apparatus 16 may be a display apparatus (e.g., a display) capable of displaying information relating to the information processing system 10. Further, the output apparatus 16 may be a speaker or the like capable of audio output relating to the information processing system 10. The output apparatus 16 may be configured as a portable terminal, such as a smartphone or tablet.

The camera 18 is a camera installed in a position capable of imaging target's image (e.g., an image including the face or the iris with respect to the target). The camera 18 may be a camera mounted on a terminal (e.g., a smartphone) which the target owns. The target here is not limited to a human, but may include: an animal such as a dog, a snake and the like; and a robot and the like. The camera 20 may be a camera for taking still images or may be a camera for taking videos. The camera 20 may be configured as a visible light camera or a near infrared camera.

In FIG. 1, an example of the information processing system 10 configured to include a plurality of apparatuses has been exemplified, but all or part of their functions may be realized by one apparatus (the information processing apparatus). The information processing apparatus may be configured with, for example, only the processor 11, the RAM12, and the ROM13 described above. With respect to the other components ((i.e., the storage apparatus 14, the input apparatus 15, the output apparatus 16, and the camera 18), an external apparatus connected to, for example, the information processing apparatus may comprise them. In addition, the information processing apparatus may realize a part of the arithmetic function by an external apparatus (e.g., an external server, or a cloud system, etc.).

(Functional Configuration)

Next, a functional configuration of the information processing system 10 according to the first example embodiment will be described with reference to FIG. 2. FIG. 2 is a block diagram showing the functional configuration of the information processing system according to the first example embodiment.

Figure 2:
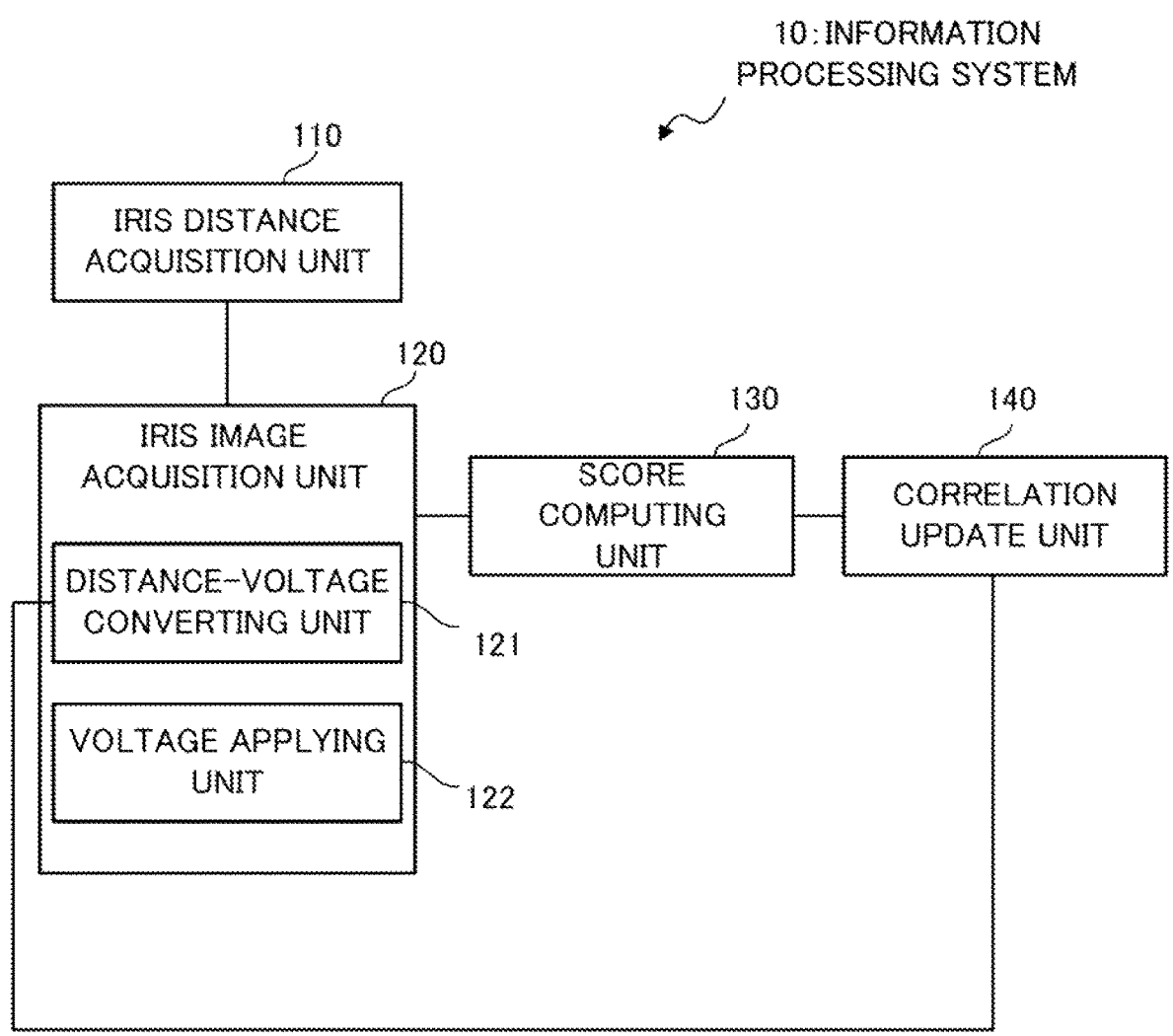
FIG. 2 is a block diagram showing a functional configuration of an information processing system according to the first example embodiment.

As shown in FIG. 2, the information processing system 10 according to the first example embodiment is configured to comprise an iris distance acquisition unit 110, an iris image acquisition unit 120, a score computing unit 130, and a correlation update unit 140 as components for realizing the functions of the information processing system 10. Each of the iris distance acquisition unit 110, the iris image acquisition unit 120, the score computing unit 130, and the correlation update unit 140 may be a processing block realized, for example, by the processor 11 described above (see FIG. 1). The iris image acquisition unit 120 may acquire an iris image using the camera 18 described above.

The iris distance acquisition unit 110 is configured so as to specify an iris area containing the iris of the target from a visible-light image of target. As for the method of specifying the iris area, since it is possible to appropriately adopt already-existing techniques, a detailed description thereof will be omitted. The iris distance acquisition unit 110 is further configured so as to acquire the iris distance, which is a distance to the iris area specified. The iris distance acquisition unit 110 may be configured to acquire the iris distance using, for example, an image of the specified iris distance and a range sensor which has been calibrated. The iris distance may be acquired as a distance from the range sensor to the iris area, or may be acquired as a distance from a camera for imaging the visible-light image or the iris image to be described later to the iris area. The iris distance data acquired at the iris distance acquisition unit 110 is outputted to the iris image acquisition unit 120.

The iris image acquisition unit 120 is configured so as to acquire the iris image of the target (i.e., an image containing the iris of the target). The iris image may be acquired, for example, as a near-infrared image. In this instance, the iris image acquisition unit 120 may be configured so as to emit near-infrared radiation to the target. The iris image acquisition unit 120 is configured so as to vary the focal length based on the iris distance acquired at the iris distance acquisition unit 110. More specifically, the iris image acquisition unit 120 is configured to change the focal length when the iris image is taken by applying a control voltage corresponding to the iris distance. The iris image acquisition unit 120 may be configured so as to acquire the iris image using, for example, a camera comprising a liquid lens, a variable focus lens, or the like. The iris image acquisition unit 120 comprises a distance-voltage converting unit 121 and a voltage applying unit 122 as components for changing the focal length.

The distance-voltage converting unit 121 is configured so as to convert the iris distance acquired at the iris distance acquisition unit 110 to the voltage value of the control voltage. That is, the distance-voltage converting unit 121 is configured so as to acquire from the iris distance acquired at the iris distance acquisition unit 110, the voltage value for realizing appropriate focal length corresponding to the iris distance. The distance-voltage converting unit 121 stores correlation between the iris distance and the control voltage and acquires from the correlation, the voltage value of the control voltage corresponding to the iris distance. The correlation between the iris distance and the control voltage may be stored, for example, as a mathematical formula, or as a look-up table or a map. As will be described later, the correlation between the iris distance and the control voltage is stored as updatable. The distance-voltage converting unit 121 is configured so as to output data relating to the voltage value of the control voltage corresponding to the iris distance to the voltage applying unit 122.

The voltage applying unit 122 is configured so as to output the control voltage having the voltage value acquired at the distance-voltage converting unit 121. The control voltage outputted by the voltage applying unit 122 is applied to a lens system including a liquid lens, a variable focus lens, or the like, thereby changing the focal length at a moment when the iris image is taken.

The score computing unit 130 is configured so as to calculate scores based on the iris image acquired at the iris image acquisition unit 120. Here, the "score" is a score relating to deviation of focus in the iris image. For example, the score may be calculated high when the image is taken in an in-focus state (i.e., a state in which the deviation is small), and the score may be calculated low when the image is taken in an out-of-focus state (i.e., a state in which the deviation is large). The deviation of the focus indicated by the score is not only the one when viewed by human eyes, but also the deviation may be the one when viewed from apparatuses. Therefore, even if the iris image is in focus when viewed from human eyes, the score may be calculated low when the iris image that is out of focus when viewed from apparatuses (i.e. the iris image that would make problems when used by apparatuses). Similarly, even if the iris image is out-of-focus when viewed from human eyes, the score may be calculated high when the iris image is in focus when viewed from apparatuses (i.e., the iris image that does not make problems when handled by apparatuses). In such cases, the score computing unit 130 may calculate, for example, an authentication score used for iris authentication (i.e., the score for determining whether authentication is successful or failed).

The specific calculation method of the score is not particularly limited, and the score computing unit 130 may calculate the score by appropriately adopting already-existing techniques. The score computing unit 130 may calculate the score from the iris image itself, or may calculate the score based on the feature amount extracted from the iris image. In addition, the score computing unit 130 may calculate the score from a plurality of iris images. For example, the score computing unit 130 may extract the feature amounts from a plurality of images that have been continuously taken and calculate the score by matching the feature amounts with each other with respect to anteroposterior images. In this event, matching out-of-focus images with each other makes the score low. On the other hand, matching in-focus images with each other makes the score high.

The correlation update unit 140 is configured so as to update the correlation between the iris distance and the control voltage, the correlation being stored in the distance-voltage converting unit 121. That is, the correlation update unit 140 is configured so as to rewrite the correlation stored in advance to a new one. Therefore, after the correlation update unit 140 updates the correlation, the conversion from the iris distance to the voltage value is performed based on the updated correlation. In particular, the correlation update unit 140 is configured so as to update the correlation based on the score calculated at the score computing unit 130. For example, the correlation update unit 140 may update the correlation so that the score calculated at the score computing unit 130 is made higher. That is, the correlation update unit 140 may update the correlation between the iris distance and the control voltage so that an in-focus iris image can be acquired at the iris image acquisition unit 120. Specific examples of updating the correlation will be described in detail in other example embodiments to be described later.

(Flow of Operation)

Next, referring to FIG. 3, a flow of operation by the information processing system 10 according to the first example embodiment will be described. FIG. 3 is a flowchart showing the flow of operation by the information processing system according to the first example embodiment.

Figure 3:
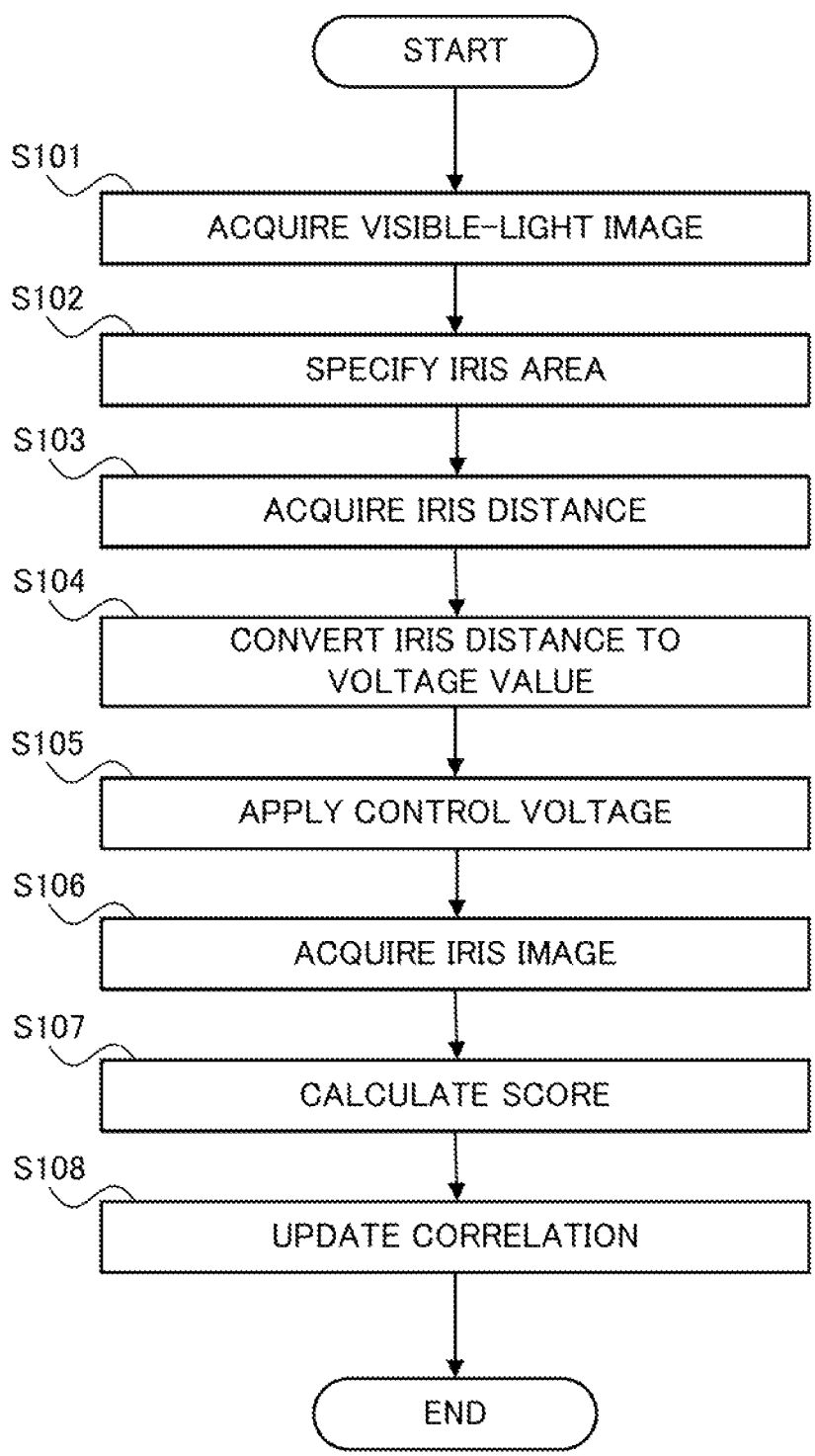
FIG. 3 is a flowchart showing a flow of operation by an information processing system according to the first example embodiment.

As shown in FIG. 3, when the information processing system 10 according to the first example embodiment operates, first, the iris distance acquisition unit 110 acquires the visible-light image of target (step S101). The iris distance acquisition unit 110 then specifies the iris area from the visible-light image of target (step S102). Then, the iris distance acquisition unit 110 acquires the iris distance, which is the distance to the iris area specified (step S103).

Subsequently, the distance-voltage converting unit 121 converts the iris distance acquired at the iris distance acquisition unit 110 to the voltage value of the control voltage (step S104). Then, the voltage applying unit 122 applies the control voltage having the voltage value converted by the distance-voltage converting unit 121 (step S105). The iris image acquisition unit 120 acquires the iris image of the target in a state that the focal length has been changed by the application of the control voltage (step S106).

Subsequently, the score computing unit 130 calculates the score based on the iris image acquired at the iris image acquisition unit 120 (step S107). Then, the correlation update unit 140 updates the correlation between the iris distance and the control voltage based on the score calculated at the score computing unit 130 (step S108).

(Technical Effects)

Next, technical effects obtained by the information processing system 10 according to the first example embodiment will be described.

As described in FIGS. 1 to 5, in the information processing system 10 according to the first example embodiment, the correlation between the iris distance and the control voltage is updated based on the score calculated from the iris image. Thereby, even if the correlation is inappropriate at a moment of adjusting the focal length, it can be appropriately updated to obtain an appropriate iris image. The correlation between the iris distance and the control voltage varies depending on individual difference of each lens or environmental changes (e.g., temperature change of lens itself). Therefore, it is difficult to set an optimum correlation in advance for all lenses. However, according to the information processing system 10 of the present example embodiment, since the correlation is updated based on the iris image actually acquired, an appropriate iris image can be acquired for the next time.

Second Example Embodiment

The information processing system 10 according to a second example embodiment will be described with reference to FIGS. 4 and 5. The second example embodiment differs from the first example embodiment described above only in a part of the configuration and operation of the first example embodiment, and the other parts may be the same as those of the first example embodiment. Therefore, the part that differs from the first example embodiment described above will be described in detail below, and other overlapping parts will be omitted as appropriate.

(Functional Configuration)

First, referring to FIG. 4, a functional configuration of the information processing system 10 according to the second example embodiment will be described. FIG. 4 is a block diagram showing the functional configuration of the information processing system according to the second example embodiment. In FIG. 4, the reference signs same in FIG. 2 are given to the components similar to in FIG. 2 respectively.

Figure 4:
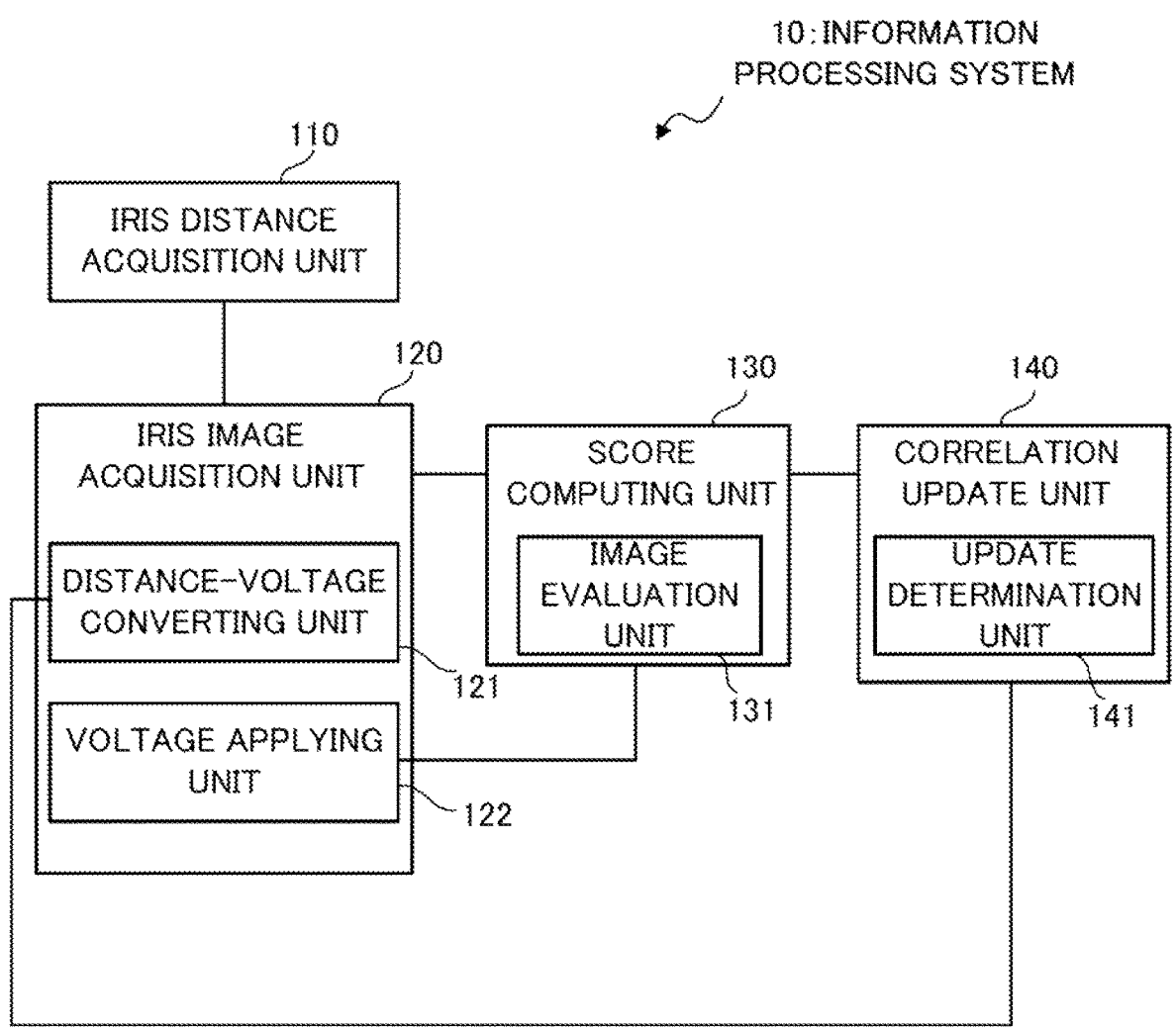
FIG. 4 is a block diagram showing a functional configuration of an information processing system according to the second example embodiment.

As shown in FIG. 4, the information processing system 10 according to the second example embodiment is configured to comprise an iris distance acquisition unit 110, an iris image acquisition unit 120, a score computing unit 130, and a correlation update unit 140 as components for realizing the functions of the information processing system 10. In particular, the score computing unit 130 according to the second example embodiment comprises an image evaluation unit 131. Further, the correlation update unit 140 according to the second example embodiment comprises an update determination unit 141.

The image evaluation unit 131 is configured so as to evaluate whether or not the iris image acquired by the iris image acquisition unit 120 is appropriate. Specifically, the image evaluation unit 131 is configured so as to evaluate whether or not the iris image acquired by the iris image acquisition unit 120 is an image suitable for use in updating the correlation. The image evaluation unit 131 may evaluate whether or not the iris image is appropriate using the score calculated at the score computing unit 130. For example, the image evaluation unit 131 may evaluate that the image having the score which is equal to or greater than a predetermined threshold value is appropriate, and when the score is less than the predetermined threshold value, the image evaluation unit 131 may evaluate that the image is inappropriate. The image evaluation unit 131 may be configured to instruct the iris image acquisition unit 120 to acquire a new iris image when the iris image is evaluated as inappropriate one. In such cases, the image evaluation unit 131 may output the instruction to acquire a new iris image by changing the voltage value of the control voltage.

The update determination unit 141 is configured so as to determine whether or not the correlation needs to be updated. The update determination unit 141 may determine whether or not the correlation needs to be updated by, for example, comparing: the voltage value calculated from the correlation stored in advance in the distance-voltage converting unit 121; and the voltage value corresponding to the image evaluated as appropriate one at the image evaluation unit 131 (e.g., the image having the highest score). Specifically, the update determination unit 141 may determine that it is necessary to update the correlation when a difference between the voltage value calculated from the original correlation and the voltage value corresponding to the image evaluated as appropriate one, exceeds a predetermined value. On the other hand, the update determination unit 141 may determine that it is unnecessary to update the correlation, when the difference between the voltage value calculated from the original correlation and the voltage value corresponding to the image evaluated as appropriate one, does not exceed the predetermined value.

(Flow of Operation)

Next, referring to FIG. 5, a flow of operation by the information processing system 10 according to the second example embodiment will be described. FIG. 5 is a flowchart illustrating the flow of operation by the information processing system according to the second example embodiment. In FIG. 5, the reference signs same in FIG. 3 are given to the processes similar to in FIG. 3 respectively.

Figure 5:
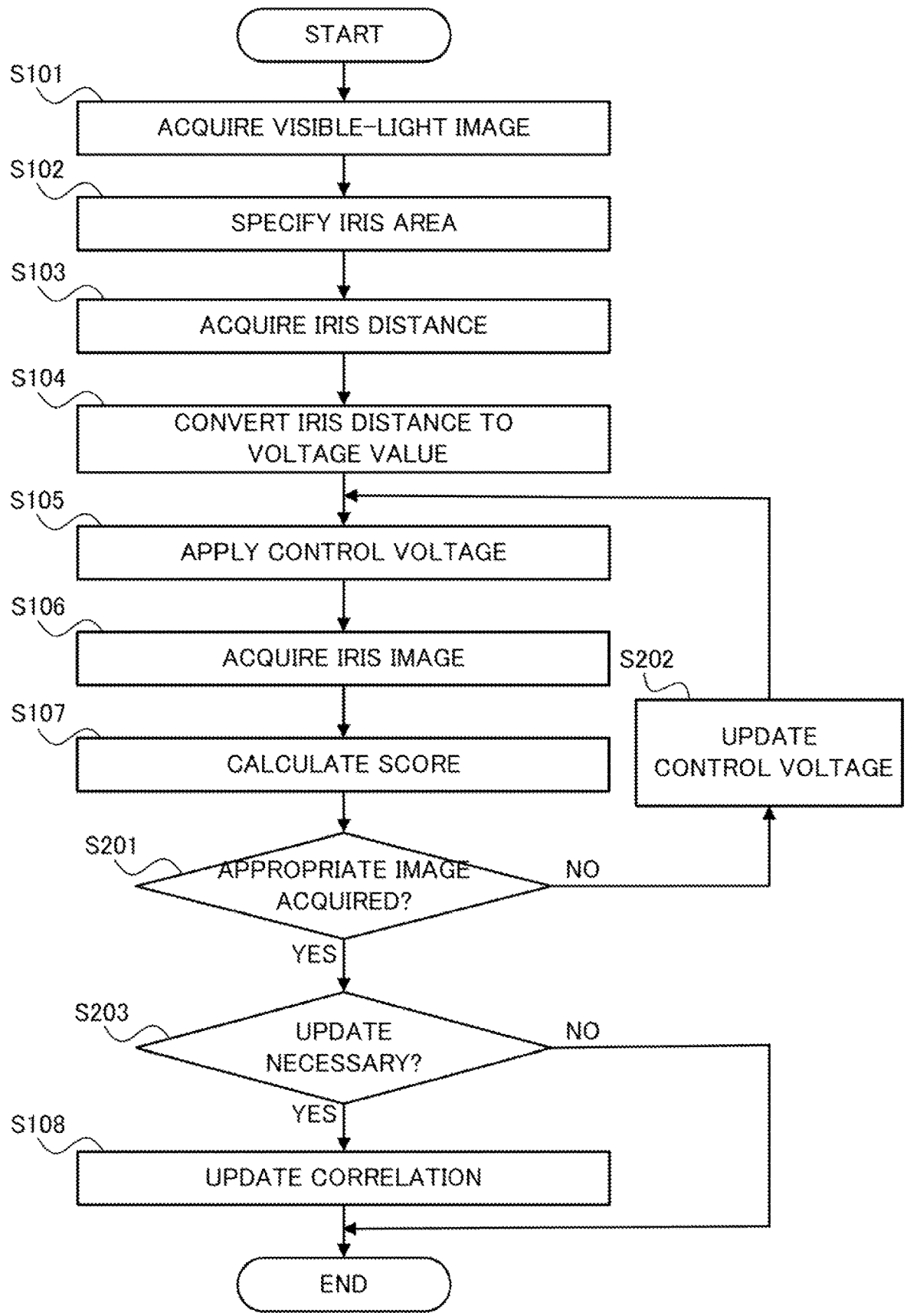
FIG. 5 is a flowchart showing a flow of operation by an information processing system according to the second example embodiment.

As shown in FIG. 5, when the information processing system 10 according to the second example embodiment operates, first, the iris distance acquisition unit 110 acquires the visible-light image of target (step S101). The iris distance acquisition unit 110 then specifies the iris area from the visible-light image of target (step S102). Then, the iris distance acquisition unit 110 acquires the iris distance, which is the distance to the iris area specified (step S103).

Subsequently, the distance-voltage converting unit 121 converts the iris distance acquired at the iris distance acquisition unit 110 to the voltage value of the control voltage (step S104). Then, the voltage applying unit 122 applies the control voltage having the voltage value converted at the distance-voltage converting unit 121 (step S105). The iris image acquisition unit 120 acquires the iris image of the target in a state that the focal length has been changed by the application of the control voltage (step S106).

Subsequently, the score computing unit 130 calculates the score based on the iris image acquired at the iris image acquisition unit 120 (step S107). In the second example embodiment, the image evaluation unit 131 evaluates whether or not an appropriate image has been acquired at the iris image acquisition unit 120 (step S201). When it is evaluated that an appropriate image has not been acquired (step S201: NO), the voltage value of the control voltage applied by the voltage applying unit 122 is updated (step S202), and processing is started again from step S105. The update of the voltage value may be performed so that the variation value is within a predetermined range (e.g., a value smaller than the width of depth of field).

On the other hand, when it is evaluated that an appropriate image has been acquired (step S201: YES), the update determination unit 141 determines whether or not it is necessary to update the correlation (step S203). Then, when it is determined that it is necessary to update the correlation (step S203: YES), the correlation update unit 140 updates the correlation between the iris distance and the control voltage based on the score calculated at the score computing unit 130 (step S108). On the other hand, when it is determined that it is unnecessary to update the correlation (step S203: NO), the correlation update unit 140 does not update the correlation between the iris distance and the control voltage (i.e., the processing of step S108 is skipped).

(Technical Effects)

Next, technical effects obtained by the information processing system 10 according to the second example embodiment will be described.

As described in FIGS. 4 and 5, in the information processing system 10 according to the second example embodiment, the iris image is repeatedly taken until an appropriate iris image can be acquired. Thereby, it is possible to prevent such a situation that only an improper iris image is taken and consequently the correlation cannot be updated. Further, in the information processing system 10 according to the second example embodiment, only when it is determined that the update is necessary, the correlation is updated. This prevents the correlation from being updated even though the update is unnecessary. Therefore, it is possible to reduce processing burden required for updating the correlation.

Third Example Embodiment

The information processing system 10 according to a third example embodiment will be described with reference to FIGS. 6 and 7. The third example embodiment differs from the above-described first and second example embodiments in a part of the configuration and operation thereof, and the other parts may be the same as those of the first and 2 example embodiments. Therefore, the part that differs from the example embodiments described above will be described in detail below, and the other overlapping parts will be omitted as appropriate.

(Functional Configuration)

First, referring to FIG. 6, a description will be given of a functional configuration of the information processing system 10 according to the third example embodiment. FIG. 6 is a block diagram illustrating the functional configuration of the information processing system according to the third example embodiment. In FIG. 6, the reference signs same in FIG. 2 are given to the components similar to in FIG. 2 respectively.

Figure 6:
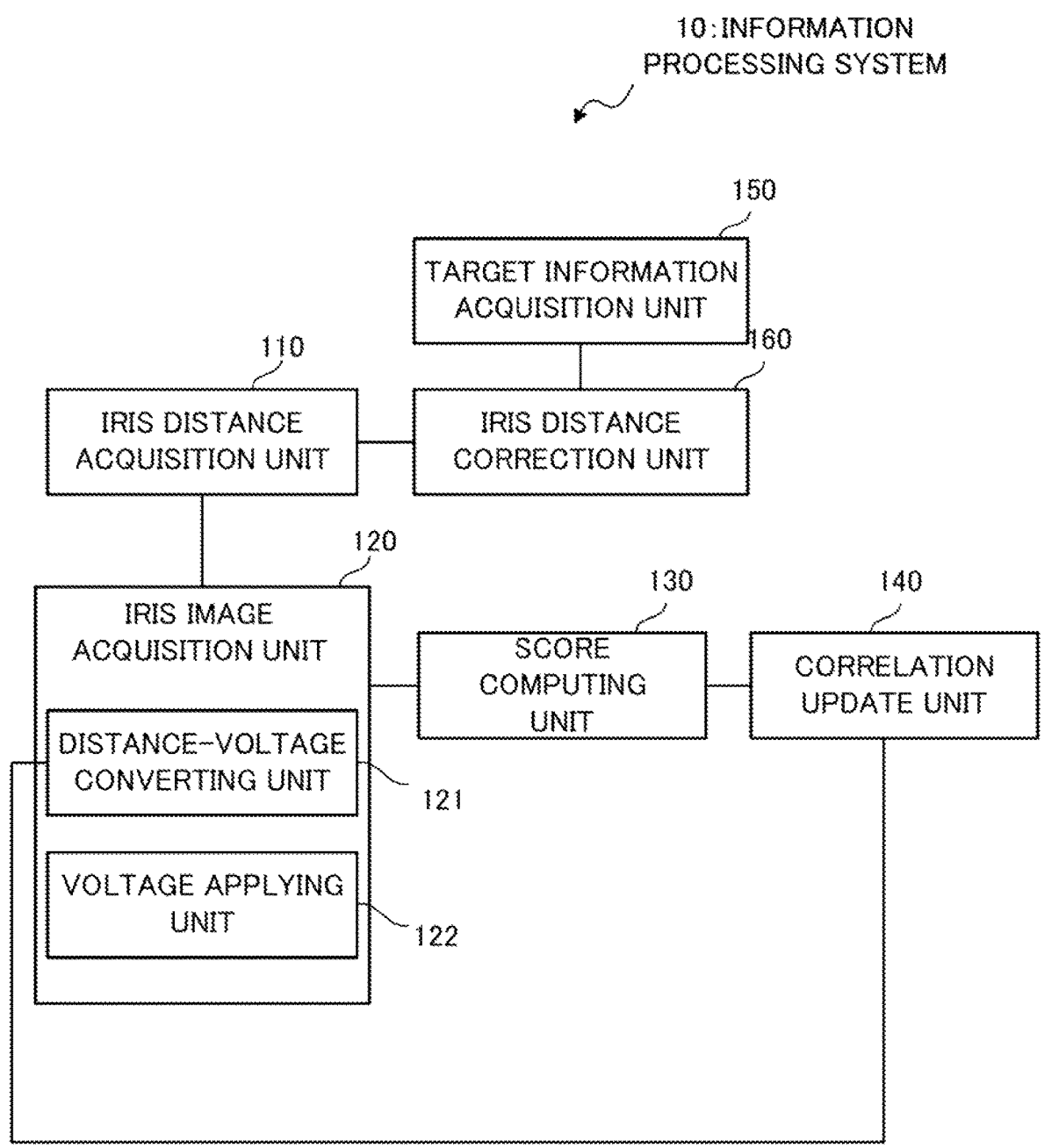
FIG. 6 is a block diagram showing a functional configuration of an information processing system according to the third example embodiment.

As shown in FIG. 6, the information processing system 10 according to the third example embodiment comprises an iris distance acquisition unit 110, an iris image acquisition unit 120, a score computing unit 130, a correlation update unit 140, a target information acquisition unit 150, and an iris distance correction unit 160 as components for realizing the functions of the information processing system 10. That is, the information processing system 10 according to the third example embodiment is configured to further comprise, in addition to the configuration of the first example embodiment (see FIG. 2), the target information acquisition unit 150, and the iris distance correction unit 160. Each of the target information acquisition unit 150 and the iris distance correction unit 160 may be a processing block realized by, for example, the processor 11 described above (see FIG. 1).

The target information acquisition unit 150 is configured so as to acquire target information from the target that acquires the visible-light image. The "target information" here is information about the elements (e.g., with or without of eyeglasses, density or length of eyelashes, depth of clear-cut features, etc.) that have an affect on acquiring the iris distance at the iris distance acquisition unit 110. The target information acquisition unit 150, for example, may acquire the target information by analyzing the visible-light image, and/or may acquire the target information from various kinds of sensors or the like. Alternatively, the target information acquisition unit 150 may acquire the target information by input operations of the target. The target information acquisition unit 150 may acquire more than one type of target information. The target information acquired at the target information acquisition unit 150 is outputted to the iris distance correction unit 160.

The iris distance correction unit 160 is configured so as to correct the distance which is acquired at the iris distance acquisition unit 110 based on the target information acquired at the target information acquisition unit 150. Specifically, the iris distance correction unit 160 is configured so as to correct the iris distance to a more accurate value based on the target information. The iris distance correction unit 160 may be configured to correct the iris distance at a moment after the acquisition at the iris distance acquisition unit 110, or, at a moment of the acquisition at the iris distance acquisition unit 110, the iris distance correction unit 160 may substantially correct the iris distance to be acquired (for example, by changing the acquiring method of the iris image). For example, the iris distance correction unit 160 may correct the iris distance, when the target information indicating that the target is wearing eyeglasses has been acquired, to a distance to the iris existing at the back of the eyeglasses (e.g., may add to the acquired iris distance, a few centimeters corresponding to the depth from the eyeglasses). Thereby, it is possible to prevent the eyeglasses position from being falsely recognized as the iris position.

(Flow of Operation)

Next, referring to FIG. 7, a flow of operation by the information processing system 10 according to the third example embodiment will be described. FIG. 7 is a flowchart showing the flow of operation by the information processing system according to the third example embodiment. In FIG. 7, the reference signs same in FIG. 3 are given to the processes similar to in FIG. 3 respectively.

Figure 7:
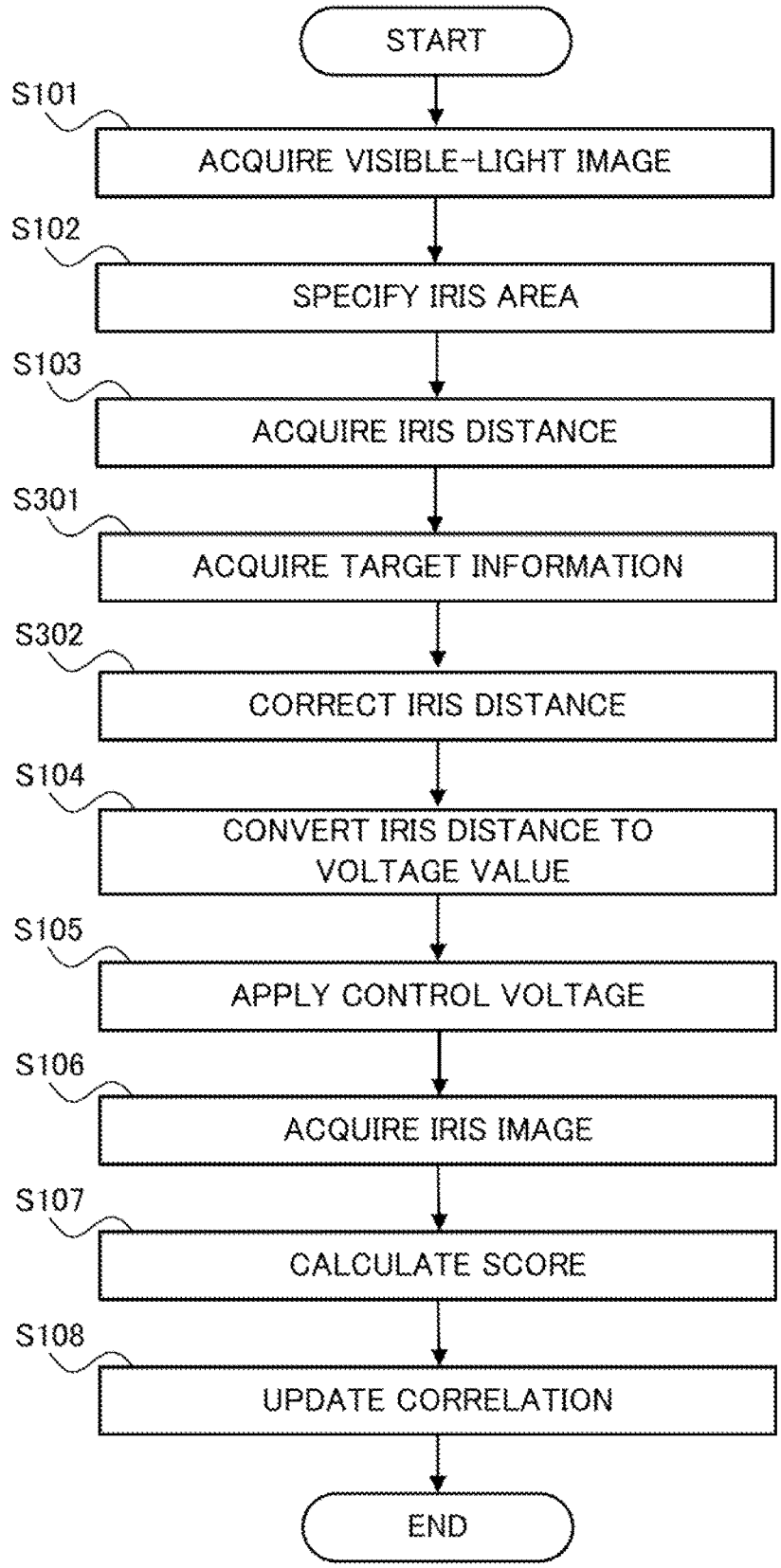
FIG. 7 is a flowchart showing a flow of operation by an information processing system according to the third example embodiment.

As shown in FIG. 7, when the information processing system 10 according to the third example embodiment operates, first, the iris distance acquisition unit 110 acquires the visible-light image of target (step S101). The iris distance acquisition unit 110 then specifies the iris area from the visible-light image of target (step S102). Then, the iris distance acquisition unit 110 acquires the iris distance, which is the distance to the iris area specified (step S103).

Subsequently, the target information acquisition unit 150 acquires the target information (step S301). Then, the iris distance correction unit 160 corrects the iris distance which is acquired at the iris distance acquisition unit 110, based on the target information acquired at the target information acquisition unit 150 (Step S302). The processes of steps S301 and S302 may be implemented in parallel with, or around the same time of, the processes from step S101 to step S103 described above.

Subsequently, the distance-voltage converting unit 121 converts the corrected iris distance to the voltage value of the control voltage (step S104). Then, the voltage applying unit 122 applies the control voltage having the voltage value converted at the distance-voltage converting unit 121 (step S105). The iris image acquisition unit 120 acquires the iris image of the target in a state that the focal length has been changed by the application of the control voltage (step S106).

Subsequently, the score computing unit 130 calculates the score based on the iris image acquired at the iris image acquisition unit 120 (step S107). Then, the correlation update unit 140 updates the correlation between the iris distance and the control voltage based on the score calculated at the score computing unit 130 (step S108).

(Technical Effects)

Next, technical effects obtained by the information processing system 10 according to the third example embodiment will be described.

As described in FIGS. 6 and 7, in the information processing system 10 according to the third example embodiment, the iris distance is corrected based on the target information. Thereby, it is possible to update the correlation more appropriately, because more accurate iris distance can be used in comparison with a case that the correction is not performed.

Fourth Example Embodiment

The information processing system 10 according to a fourth example embodiment will be described with reference to FIGS. 8 and 9. The fourth example embodiment differs from the first to third example embodiments described above only in a part of the configuration and operation thereof, and the other parts may be the same as those of the first to third example embodiments. Therefore, the part that differs from the example embodiments described above will be described in detail below, and the other overlapping parts will be omitted as appropriate.

(Functional Configuration)

First, referring to FIG. 8, a description will be given of a functional configuration of the information processing system 10 according to the fourth example embodiment. FIG. 8 is a block diagram illustrating the functional configuration of the information processing system according to the fourth example embodiment. In FIG. 8, the reference signs same in FIG. 2 are given to the components similar to in FIG. 2 respectively.

Figure 8:
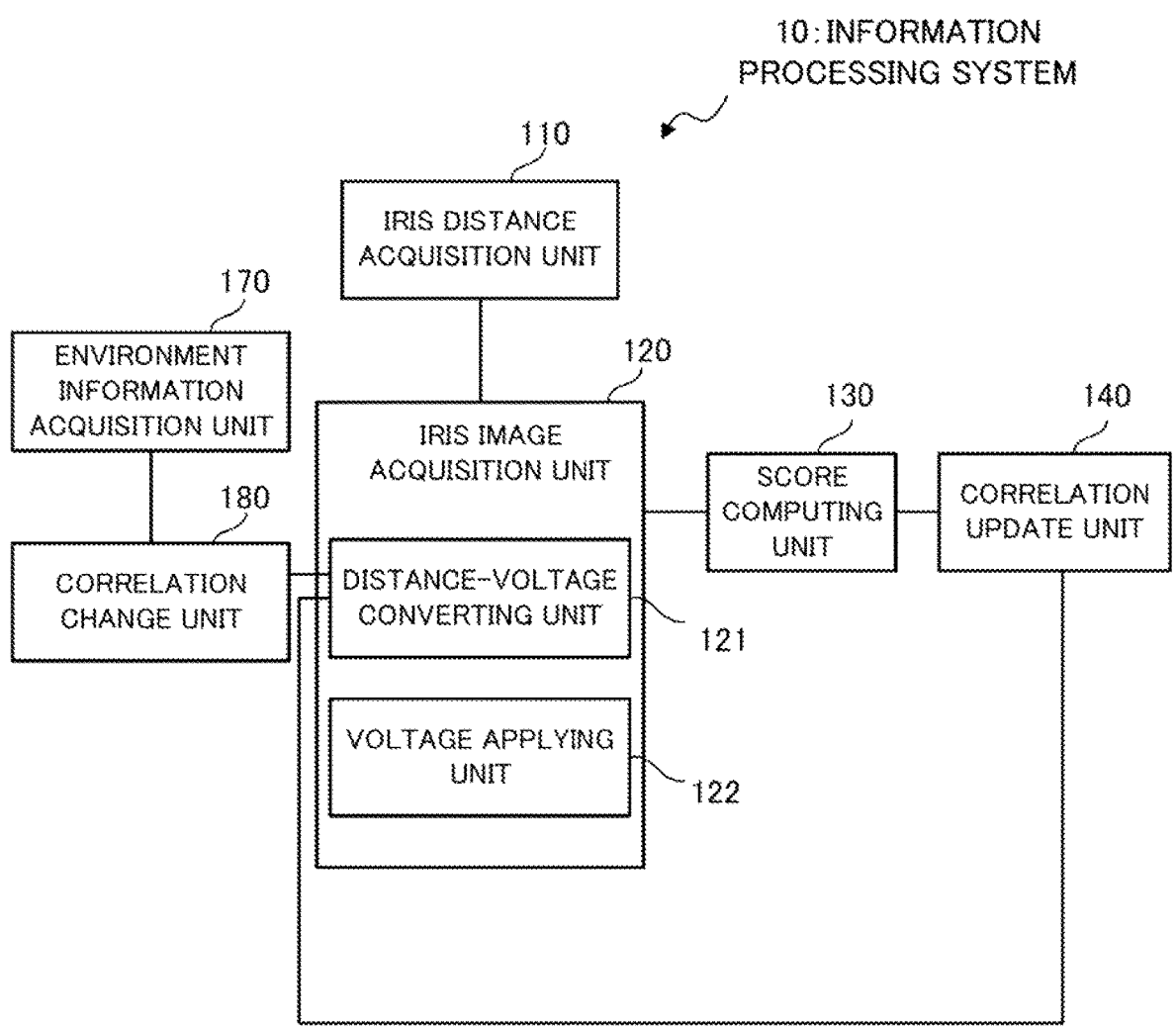
FIG. 8 is a block diagram showing a functional configuration of an information processing system according to the fourth example embodiment.

As shown in FIG. 8, the information processing system 10 according to the fourth example embodiment comprises an iris distance acquisition unit 110, an iris image acquisition unit 120, a score computing unit 130, a correlation update unit 140, an environment information acquisition unit 170, and a correlation change unit 180 as components for realizing the functions of the information processing system 10. That is, the information processing system 10 according to the fourth example embodiment is configured to further comprise, in addition to the configuration of the first example embodiment (see FIG. 2), the environment information acquisition unit 170, and the correlation change unit 180. Each of the environment information acquisition unit 170 and the correlation change unit 180 may be a processing block realized by, for example, the processor 11 described above (see FIG. 1).

The environment information acquisition unit 170 is configured so as to acquire the environment information on the environment at a moment of acquisition of the iris image. The "environment information" here is information on the environment that would affect correlation between the iris distance and the control voltage. The environment information may be, for example, information indicating the temperature of the surround of the lens, information indicating the temperature of the lens itself, and/or the like. The environment information acquisition unit 170 may acquire the environment information using, for example, various kinds of sensors. The environment information acquisition unit 170 may acquire more than one type of environment information. The environment information acquired at the environment information acquisition unit 170 is outputted to the correlation change unit 180.

The correlation change unit 180 is configured to change the correlation to be used for converting the iris distance to the voltage value of the control voltage, based on the environment information acquired at the environment information acquisition unit 170. Here, "change" is, different from "update" performed by the correlation update unit 140, temporary. Specifically, the correlation change unit 180 only changes the correlation to be used with respect to the current target for converting the iris distance to the voltage value of the control voltage. The correlation change unit 180 does not newly rewrite the correlation which the distance-voltage converting unit 121 stores. Accordingly, if the target changes, the correlation basically returns to the one previously stored. For example, when the distance-voltage converting unit 121 stores a plurality of correlations, the correlation change unit 180 may perform operation of selecting the correlation to be used at the moment out of the plurality of correlations. More specifically, when the distance-voltage converting unit 121 stores a table indicating the correlation for a case the temperature is high and another table indicating the correlation for a case the temperature is low, the correlation change unit 180 may perform operation of selecting which table to use based on the environment information (here, the information indicating the temperature).

(Flow of Operation)

Next, referring to FIG. 9, a flow of operation by the information processing system 10 according to the fourth example embodiment will be described. FIG. 9 is a flowchart showing the flow of operation by the information processing system according to the fourth example embodiment. In FIG. 9, the reference signs same in FIG. 3 are given to the processes similar to in FIG. 3 respectively.

Figure 9:
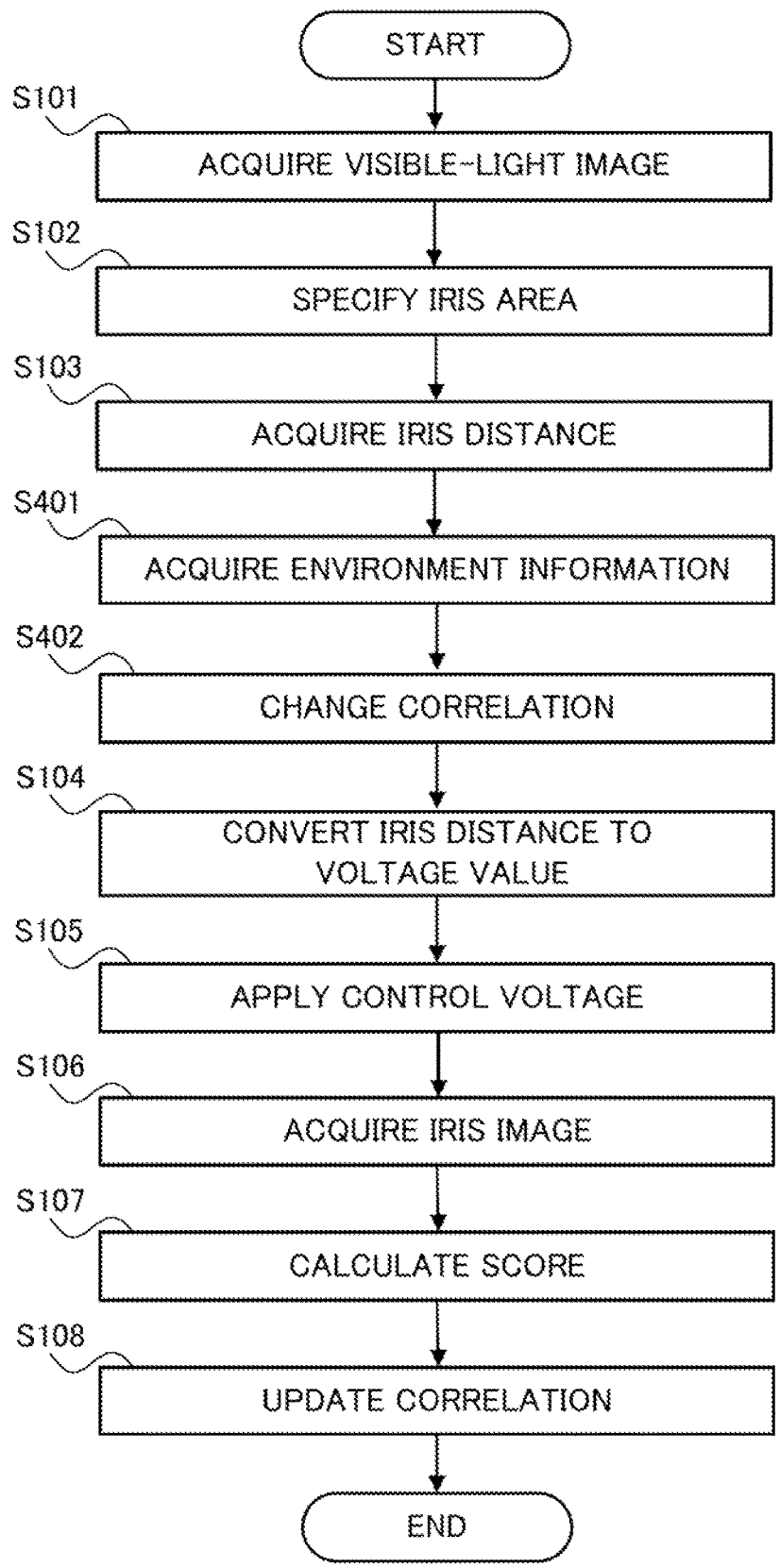
FIG. 9 is a flowchart showing a flow of operation by an information processing system according to the fourth example embodiment.

As shown in FIG. 9, when the information processing system 10 according to the fourth example embodiment operates, first, the iris distance acquisition unit 110 acquires the visible-light image of target (step S101). The iris distance acquisition unit 110 then specifies the iris area from the visible-light image of target (step S102). Then, the iris distance acquisition unit 110 acquires the iris distance, which is the distance to the iris area specified (step S103).

Subsequently, the environment information acquisition unit 170 acquires the environment information (step S401). Then, correlation change unit 180 changes the correlation based on the environment information acquired at the environment information acquisition unit 170 (step S402). The processes of steps S401 and S402 may be implemented in parallel with, or around the same time of, the processes from step S101 to step S103 described above.

Subsequently, the distance-voltage converting unit 121 converts the iris distance acquired at the iris distance acquisition unit 110 to the voltage value of the control voltage (step S104). Then, the voltage applying unit 122 applies the control voltage having the voltage value converted at the distance-voltage converting unit 121 (step S105). The iris image acquisition unit 120 acquires the iris image of the target in a state that the focal length has been changed by the application of the control voltage (step S106).

Subsequently, the score computing unit 130 calculates the score based on the iris image acquired at the iris image acquisition unit 120 (step S107). Then, the correlation update unit 140 updates the correlation between the iris distance and the control voltage based on the score calculated at the score computing unit 130 (step S108).

(Technical Effects)

Next, a description will be given of technical effects obtained by the information processing system 10 according to the fourth example embodiment.

As described in FIGS. 8 and 9, in the information processing system 10 according to the fourth example embodiment, the correlation is changed based on the environment information. Thereby, the appropriate correlation will be used, taking into account the effects of environmental changes. Consequently, it is possible to acquire a more appropriate iris image in comparison with a case without environmental data.

Fifth Example Embodiment

The information processing system 10 according to a fifth example embodiment will be described with reference to FIGS. 10 to 12. The fifth example embodiment differs from the first to fourth example embodiments described above only in a part of the configuration and operation thereof, and the other parts may be the same as those of the first to fourth example embodiments. Therefore, the part that differs from the example embodiments described above will be described in detail below, and the other overlapping parts will be omitted as appropriate.

(Functional Configuration)

First, a functional configuration of the information processing system 10 according to the fifth example embodiment will be described with reference to FIG. 10. FIG. 10 is a block diagram showing the functional configuration of the information processing system according to the fifth example embodiment. In FIG. 10, the reference signs same in FIG. 2 are given to the components similar to in FIG. 2 respectively.

Figure 10:
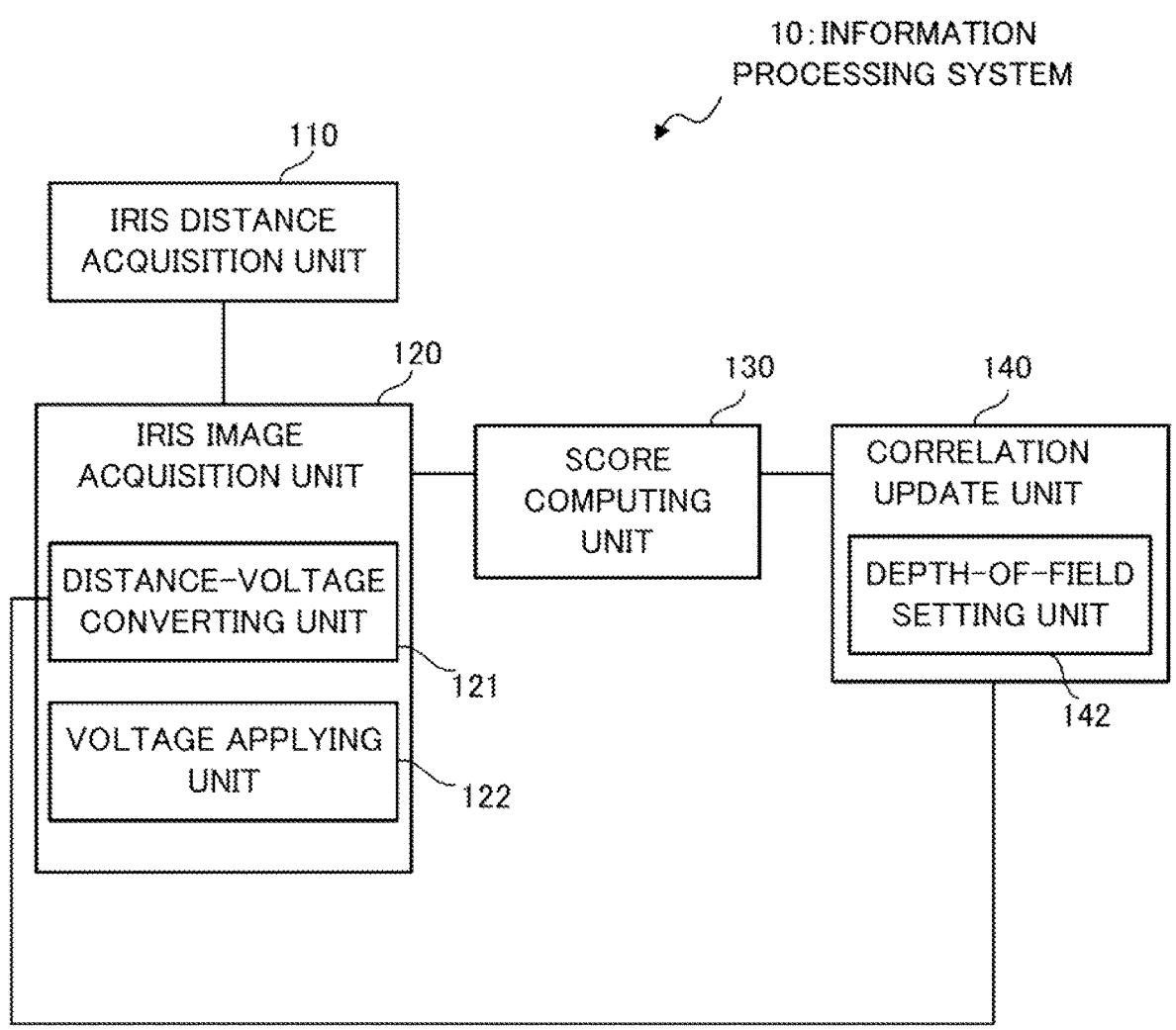
FIG. 10 is a block diagram showing a functional configuration of an information processing system according to the fifth example embodiment.

As shown in FIG. 10, the information processing system 10 according to the fifth example embodiment is configured to comprise an iris distance acquisition unit 110, an iris image acquisition unit 120, a score computing unit 130, and a correlation update unit 140 as components for realizing the functions of the information processing system 10. In particular, the correlation update unit 140 according to the fifth example embodiment comprises a depth-of-field setting unit 142.

The depth-of-field setting section 142 is configured so as to set the depth of field which is taken into account at a moment of update of the correlation. More specifically, the depth-of-field setting unit 142 sets the depth of field required for the iris authentication using the iris image as the depth of field which is taken into account at a moment of update of the correlation. The depth-of-field setting unit 142 may store the depth of field required for the iris authentication in advance or may acquire the depth of field from the outside of the system as appropriate. The required depth of field in the iris authentication may differ depending on the type of authentication. For example, the depth of field required for the 1:1 authentication may be a range narrower than the depth of field required for the 1:N authentication. If a different depth of field depending on the type of authentication type is required, the depth-of-field setting section 142 may select the depth of field corresponding to the iris authentication to be implemented at the moment from the different depth of fields. More information on the updating method of the correlation where the depth of field is taken into account will be provided later.

(Flow of Operation)

Next, referring to FIG. 11, a flow of operation by the information processing system 10 according to the fifth example embodiment will be described. FIG. 11 is a flowchart showing the flow of operation by the information processing system according to the fifth example embodiment. In FIG. 11, the reference signs same in FIG. 3 are given to the processes similar to in FIG. 3 respectively.

Figure 11:
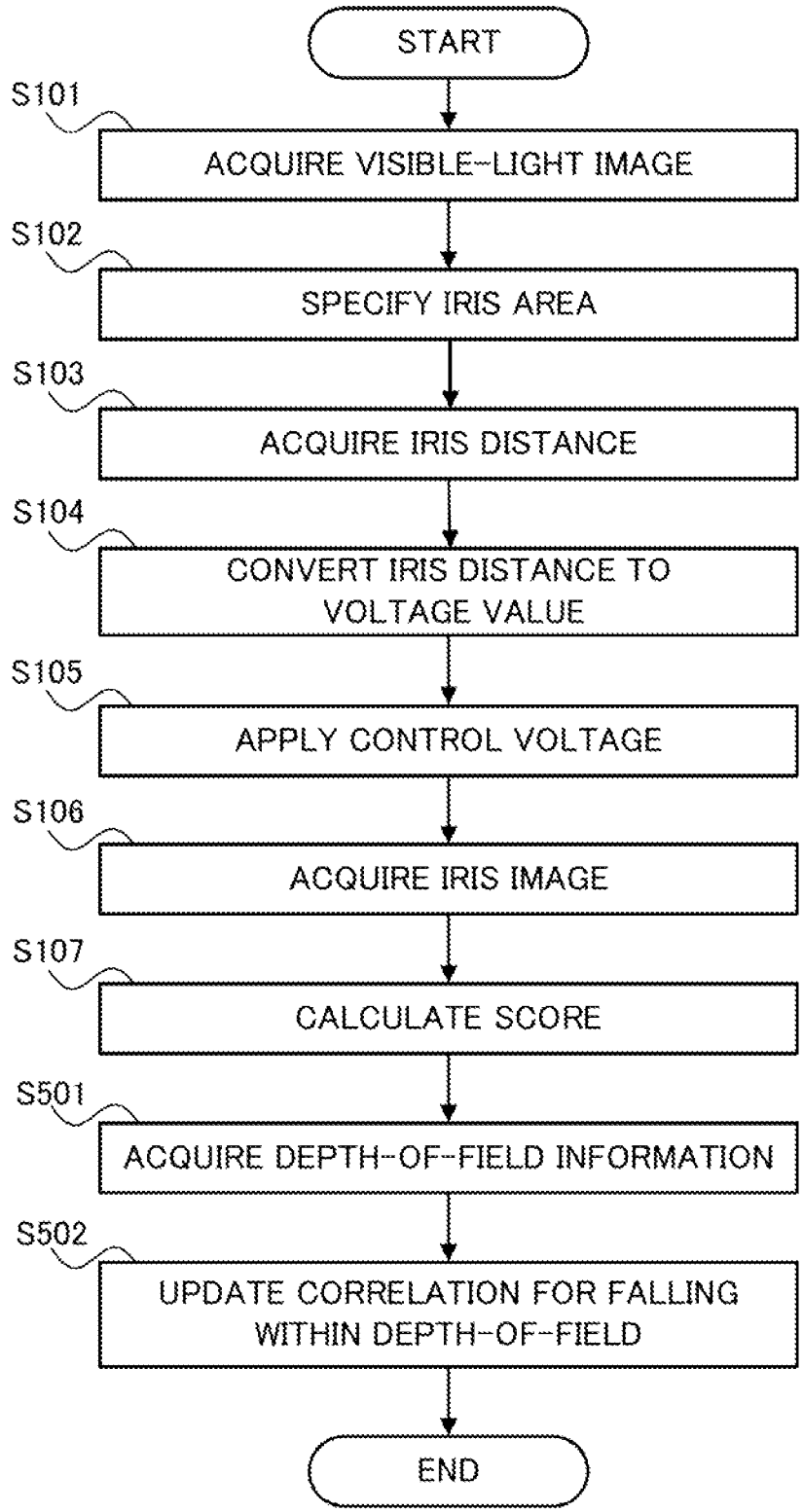
FIG. 11 is a flowchart showing a flow of operation by an information processing system according to the fifth example embodiment.

As shown in FIG. 11, when the information processing system 10 according to the fifth example embodiment operates, first, the iris distance acquisition unit 110 acquires the visible-light image of target (step S101). The iris distance acquisition unit 110 then specifies the iris area from the visible-light image of target (step S102). Then, the iris distance acquisition unit 110 acquires the iris distance, which is the distance to the iris area specified (step S103).

Subsequently, the distance-voltage converting unit 121 converts the iris distance acquired at the iris distance acquisition unit 110 to the voltage value of the control voltage (step S104). Then, the voltage applying unit 122 applies the control voltage having the voltage value converted at the distance-voltage converting unit 121 (step S105). The iris image acquisition unit 120 acquires the iris image of the target in a state that the focal length has been changed by the application of the control voltage (step S106).

Subsequently, the score computing unit 130 calculates the score based on the iris image acquired at the iris image acquisition unit 120 (step S107). Then, the depth-of-field setting unit 142 acquires information about the depth of field required for the iris authentication using the iris image acquired this time (step S501). The process of step S501 may be implemented in parallel with, or around the same time of, the processes before step S501 (the processes from step S101 to step S107).

Subsequently, the correlation update unit 140 updates the correlation between the iris distance and the control voltage based on the score calculated at the score computing unit 130. At the moment, the correlation update unit 140 updates the correlation, taking into account the depth of field acquired at the depth-of-field setting section 142. Specifically, the correlation is updated so that the deviation of updated focal length falls within the range of the depth of field acquired at the depth-of-field setting section 142 (step S502).

(Example of Updating Correlation)

Next, referring to FIG. 12, the operation at a moment of update of the correlation by the correlation update unit 140 according to the fifth example embodiment will be described with a specific example. FIG. 12 is a graph showing a specific example that the correlation is changed by the information processing system according to the fifth example embodiment.

Figure 12:
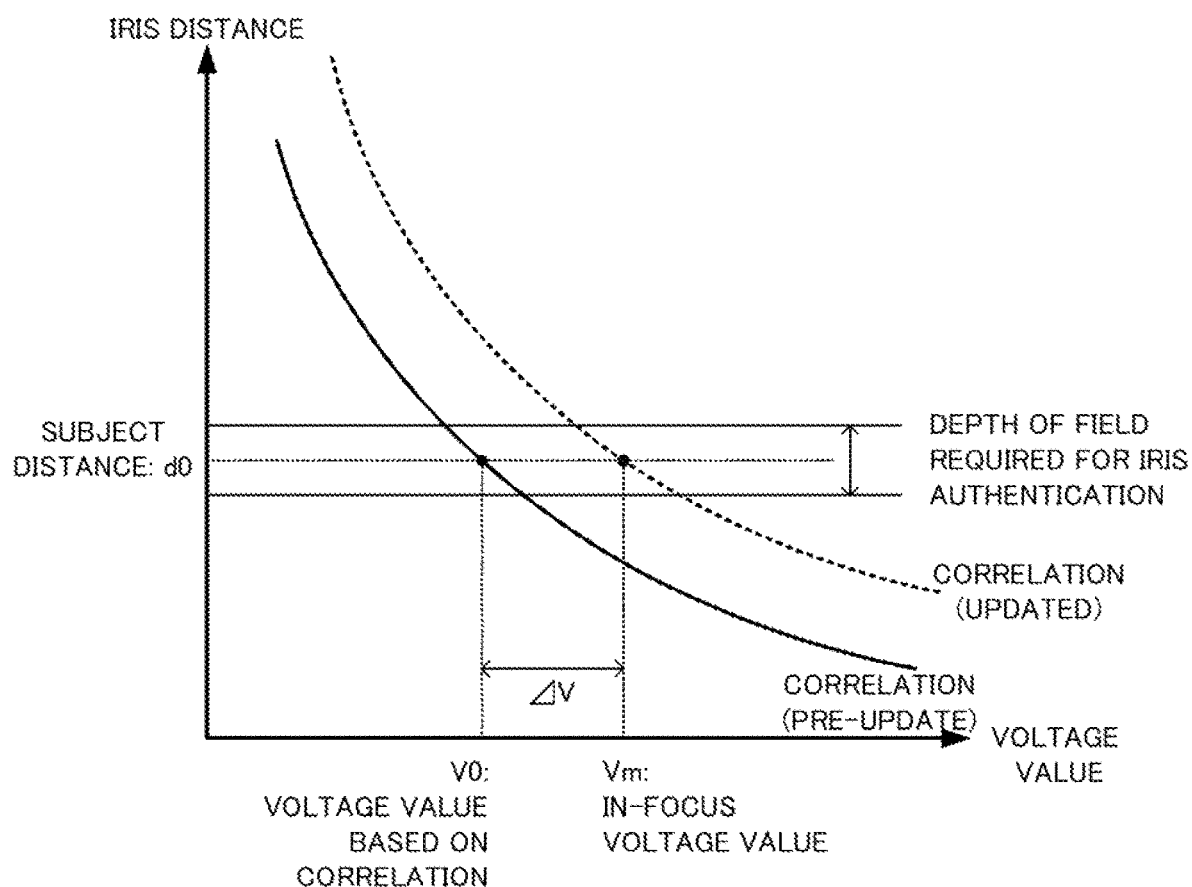
FIG. 12 is a graph showing specific change of correlation by an information processing system according to the fifth example embodiment.

As shown in FIG. 12, according to the correlation between the iris distance and the control voltage (see the straight line in the figure), the correlation being stored in advance, when the voltage value VO corresponding to the subject distance dO is applied as the control voltage, the subject (i.e., the iris of the target) falls within the range of the depth of field. However, if this correlation changes, even if the voltage value VO is applied as the control voltage, the subject will not fall within the range of the depth of field. For this reason, the correlation update unit 140 updates the correlation stored so that the correlation becomes correct when the correlation changes.

The correlation update unit 140 may update the correlation, for example, by adding an offset to the voltage value. Specifically, when the stored correlation is represented by V=f (d), the correlation is updated so as to be represented by V=f (d)+$\Delta$V. "V" is the voltage value, "d" is the distance, "f ( ) is a function of the distance and voltage value," $\Delta$V" is the offset. The value of the offset $\Delta$V can be calculated, for example, as a difference between: the voltage value VO which is calculated from the original correlation, according to the iris distance acquired at the iris distance acquisition unit 110; and the voltage value Vm corresponding to the iris image having the highest score within the iris images acquired by the iris image acquisition unit 120.

In this example embodiment, in particular, the correlation is updated so that the subject falls within the range of the depth of field required for the iris authentication after the update (see the dashed lines in the figure).

(Technical Effects)

Next, technical effects obtained by the information processing system 10 according to the fifth example embodiment will be described.

As described in FIGS. 10 to 12, in the information processing system 10 according to the fifth example embodiment, the correlation is updated taking into account the depth of field required for the iris authentication. The required depth of field for the iris authentication may differ depending on the type of authentication, as described above. Accordingly, by updating the correlation so that the depth of field falls within the depth of field required for the iris authentication actually performed, it is possible to acquire a more appropriate iris image (i.e., the iris image suitable for the iris authentication).

Sixth Example Embodiment

The information processing system 10 according to a sixth example embodiment will be described with reference to FIGS. 13 to 15. The sixth example embodiment differs from the first to fifth example embodiments described above only in a part of the configuration and operation thereof, and the other parts may be the same as those of the first to fifth example embodiments. Therefore, the part that differs from the example embodiments described above will be described in detail below, and the other overlapping parts will be omitted as appropriate.

(Display Example of Pre-Update)

First, referring to FIG. 13, a display example of pre-update of the correlation by the information processing system 10 according to the sixth example embodiment will be described. FIG. 13 is a plan view showing the display example of pre-update of the correlation by the information processing system according to the sixth example embodiment.

Figure 13:
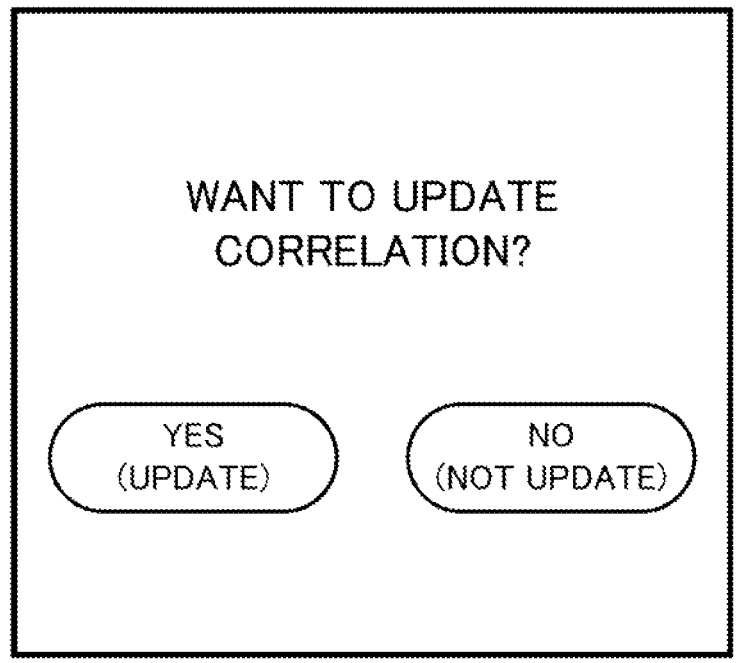
FIG. 13 is a plan view showing a display example of pre-update of correlation by an information processing system according to the sixth example embodiment.

As shown in FIG. 13, the information processing system 10 according to the sixth example embodiment may perform a display for allowing the user to determine whether or not to update the correlation, before updating the correlation. Here, with the message "WANT TO UPDATE CORRELATION?", the button "YES (UPDATE)" and the other button "NO (NOT UPDATE)" are displayed. In this situation, when the user presses the button "YES", the correlation is updated. On the other hand, when the user presses the button "NO", the correlation is not updated. In this way, it can be left to the user to judge whether or not to implement the update of correlation. In addition to the display shown in FIG. 13, the iris image (i.e., the iris image that is not in focus) taken in a state before the update or a score corresponding to the image may be displayed.

(Display Example During Update)

Next, referring to FIG. 14, a display example displayed during update of the correlation by the information processing system 10 according to the sixth example embodiment will be described. FIG. 14 is a plan view showing the display example displayed during update of the correlation by the information processing system according to the sixth example embodiment.

As shown in FIG. 14, the information processing system 10 according to the sixth example embodiment may display a notice that the correlation is being updated during the update of the correlation. Here, the message "CORRELATION NOW UPDATING . . . " is displayed along with the message "PLEAE DO NOT MOVE". This could prevent the user from moving. Accordingly, it is possible to take appropriately the iris image which is used for updating the correlation. In addition to the display shown in FIG. 14, the time required for the update of the correlation or the remaining time and/or the number of the iris images may be displayed. Alternatively, the iris image taken for updating the correlation or the like may be displayed.

(Display Example Post-Update)

Next, referring to FIG. 15, a display example of post-update of the correlation by the information processing system 10 according to the sixth example embodiment will be described. FIG. 15 is a plan view showing the display example of post-update of the correlation by the information processing system according to the sixth example embodiment.

Figure 15:
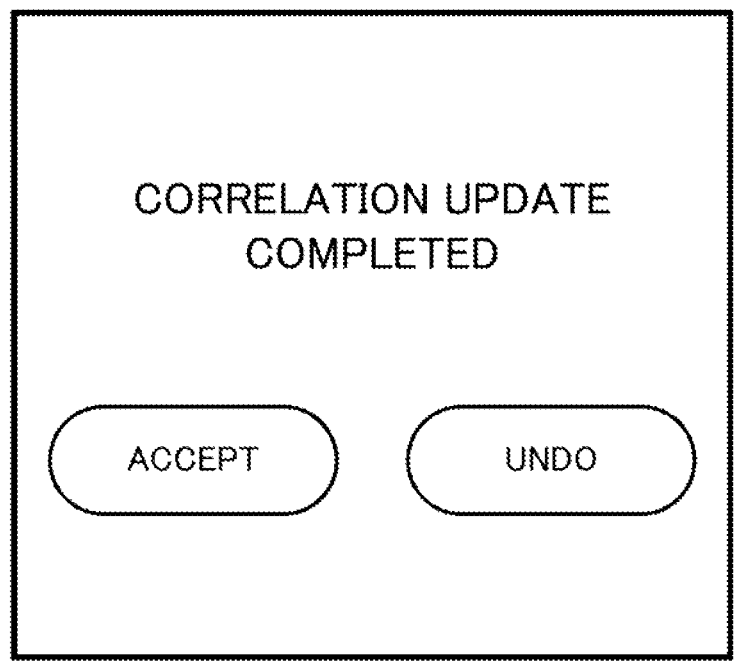
FIG. 15 is a plan view showing a display example of post-update of correlation by an information processing system according to the sixth example embodiment.

As shown in FIG. 15, the information processing system 10 according to the sixth example embodiment may display a notice that the update of correlation has been completed, after updating the correlation. Here, the message "CORRELATION UPDATE COMPLETED" is displayed with the button "ACCEPT" and the button "UNDO". If the user presses the button "ACCEPT" in this situation, the update of the correlation is confirmed. On the other hand, when the user presses the button "UNDO" button, the correlation is returned to the pre-update state. This prevents user's undesirable update of correlation from being performed. In addition to the display shown in FIG. 15, the iris image (i.e., the in-focus iris image) taken after the update, the score after the update, and/or the like may be also displayed. In addition, the images and the scores before and after the update may be displayed side by side in such a manner that the change caused by the update of correlation can be compared.
(Technical Effects)

Next, a description will be given of technical effects obtained by the information processing system 10 according to the sixth example embodiment.

As described in FIGS. 13 to 15, according to the information processing system 10 according to the sixth example embodiment, it is possible to comprehensibly notify the user of the system (e.g., the target or the system manager) of various information relating to update of correlation.

Seventh Example Embodiment

The information processing system 10 according to a seventh example embodiment will be described with reference to FIGS. 16 and 17. The seventh example embodiment differs from the first to sixth example embodiments described above only in a part of the configuration and operation thereof, and the other parts may be the same as those of the first to sixth example embodiments. Therefore, the part that differs from the example embodiments described above will be described in detail below, and the other overlapping parts will be omitted as appropriate.
(Functional Configuration)

First, referring to FIG. 16, a description will be given of a functional configuration of the information processing system 10 according to the seventh example embodiment. FIG. 16 is a block diagram illustrating the functional configuration of the information processing system according to the seventh example embodiment. In FIG. 16, the reference signs same in FIG. 2 are given to the components similar to in FIG. 2 respectively.

As shown in FIG. 4, the information processing system 10 according to the seventh example embodiment is configured to comprise an iris distance acquisition unit 110, an iris image acquisition unit 120, a score computing unit 130, and a correlation update unit 140 as components for realizing the functions of the information processing system 10. In particular, the iris image acquisition unit 120 according to the seventh example embodiment comprises a focal length acquisition unit 125 and a focal length control unit 126.

The focal length acquisition unit 125 is configured so as to acquire an appropriate focal length corresponding to the iris distance according to the iris distance acquired at the iris distance acquisition unit 110. The focal length acquisition unit 125 stores the correlation between the iris distance and the focal length, and acquires from the correlation the focal length corresponding to the iris distance. The correlation between the iris distance and the focal length may be stored, for example, as a mathematical expression, or may be stored as a look-up table or a map. The correlation between the iris distance and the focal length is stored so as to be updated as appropriate. The focal length acquisition unit 125 is configured so as to output to the focal length control unit 126, information relating to the focal length corresponding to the iris distance.

The focal length control unit 126 is configured so as to change the focal length at a moment when the iris image is taken, so that the focal length becomes the one acquired at the focal length acquisition unit 125. The control method of the focal length here is not limited to the method using the control voltage described in the example embodiments from the first to the sixth. For example, the focal length control unit 126 may control the focal length using various techniques including already existing techniques.

The correlation update unit 140 according to the seventh example embodiment is configured so as to update the correlation between the iris distance and the focal length stored by the focal length acquisition unit 125. Accordingly, after the correlation update unit 140 updates the correlation, the focal length corresponding to the iris distance is acquired based on the updated correlation. In particular, the correlation update unit 140 is configured so as to update the correlation based on the score calculated at the score computing unit 130. The correlation update unit 140 may update the correlation so that the score calculated at the score computing unit 130 is made higher. That is, the correlation update unit 140 may update the correlation between the iris distance and the focal length so that an in-focus iris image can be acquired at the iris image acquisition unit 120.
(Flow of Operation)

Next, referring to FIG. 17, a flow of operation by the information processing system 10 according to the seventh example embodiment will be described. FIG. 17 is a flowchart illustrating the flow of operation by the information processing system according to the seventh example embodiment. In FIG. 17, the reference signs same in FIG. 3 are given to the processes similar to in FIG. 3 respectively.

Figure 17:
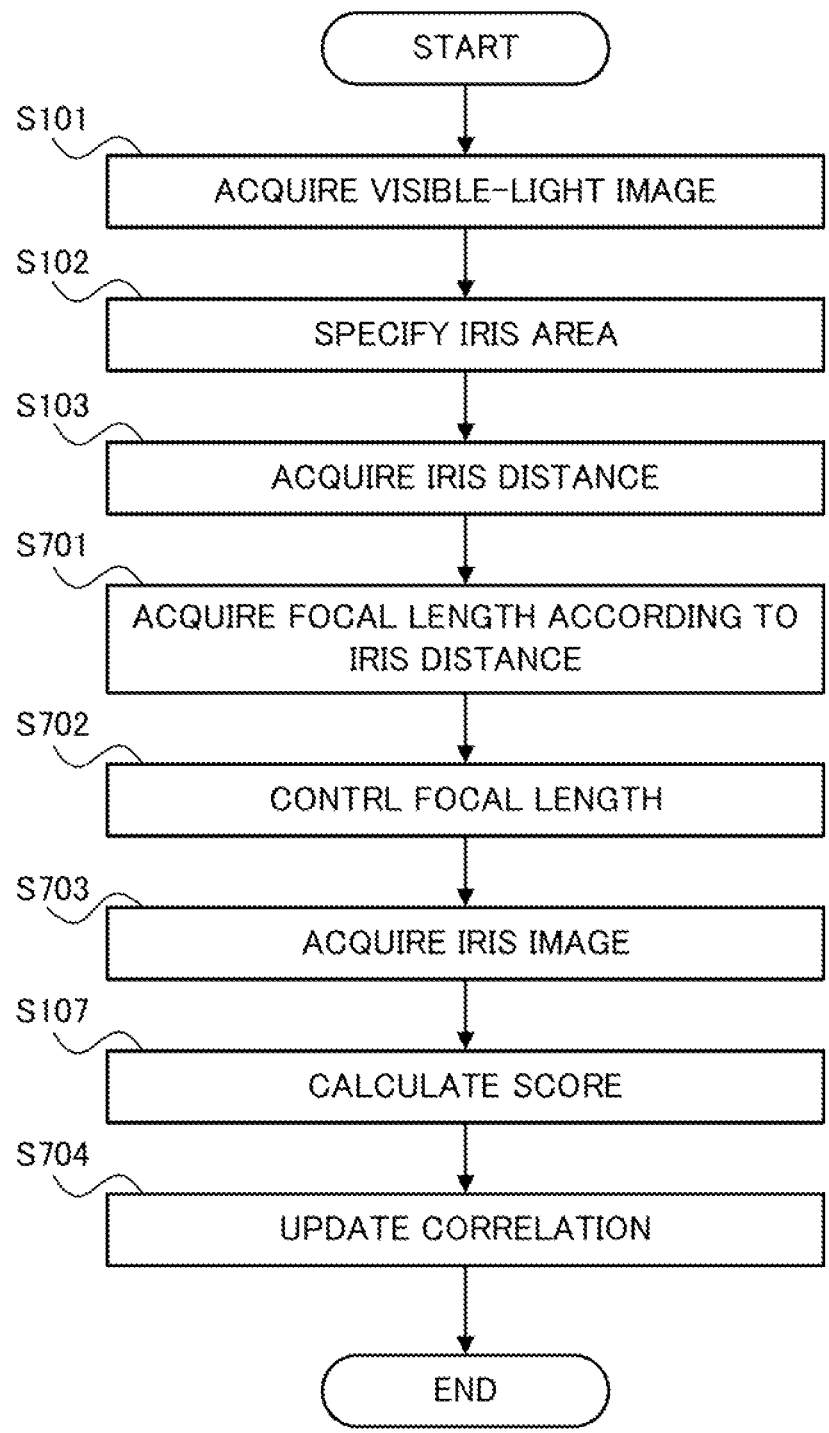
FIG. 17 is a flowchart showing the flow of operation by an information processing system according to the seventh example embodiment.

As shown in FIG. 17, when the information processing system 10 according to the seventh example embodiment operates, first, the iris distance acquisition unit 110 acquires the visible-light image of target (step S101). The iris distance acquisition unit 110 then specifies the iris area from the visible-light image of target (step S102). Then, the iris distance acquisition unit 110 acquires the iris distance, which is the distance to the iris area specified (step S103).

Subsequently, the focal length acquisition unit 125 acquires the focal length corresponding to the iris distance acquired at the iris distance acquisition unit 110 (step S701). Then, the focal length control unit 126 controls the focal length so that the focal length becomes a value acquired at the focal length acquisition unit 125 (step S702). The iris image acquisition unit 120 acquires the iris image of the target after the focal length is controlled at the focal length control unit 126 (i.e., with the focal length acquired at the focal length acquisition unit 125) (step S703).

Subsequently, the score computing unit 130 calculates the score based on the iris image acquired at the iris image acquisition unit 120 (step S107). Then, the correlation update unit 140 updates the correlation between the iris distance and the focal length based on the score calculated at the score computing unit 130 (step S704).
(Technical Effects)

Next, technical effects obtained by the information processing system 10 according to the seventh example embodiment will be described.

Figure 16:
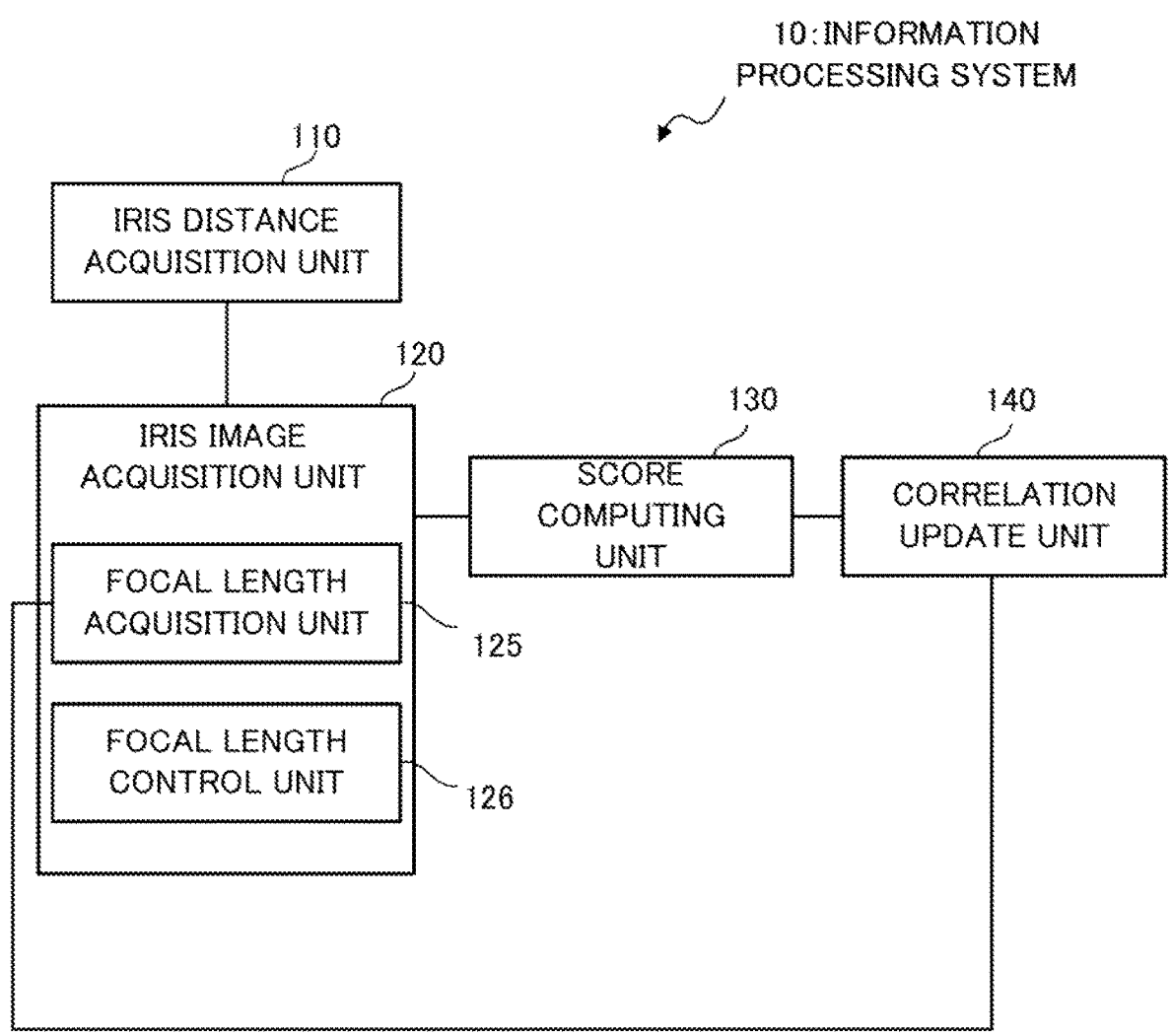
FIG. 16 is a block diagram showing a functional configuration of an information processing system according to the seventh example embodiment.

As described in FIGS. 16 and 17, in the information processing system 10 according to the seventh example embodiment, the correlation between the iris distance and the focal length is updated based on the score calculated from the iris image. Thereby, even if the correlation between the iris distance and the focal length is inappropriate, the inappropriate foal length can be updated to the appropriate one to acquire the appropriate iris image. The correlation between the iris distance and the control voltage varies depending on individual difference of each lens or environmental changes (e.g., temperature change of lens itself). Therefore, it is difficult to set an optimum correlation in advance for all lenses. However, according to the information processing system 10 of the present example embodiment, since the correlation is updated based on the iris image actually acquired, an appropriate iris image can be acquired for the next time.

Also included in the scope of each example embodiment is a processing method comprising the steps of: recording in a recording medium, a computer program to operate the configuration of each above-mentioned example embodiment so as to realize the functions of each example embodiment; reading out the computer program recorded in the recording medium as code; and implementing the computer program in a computer. In other words, a computer-readable recording medium is also included in the scope of each example embodiment. In addition, not only the recording medium where the above-mentioned computer program is recorded but also the computer program itself is included in each embodiment.

For example, a floppy disk (registered trademark), a hard disk, an optical disk, an optical magnetic disk, a CD-ROM, a magnetic tape, a non-volatile memory cards and a ROM can be each used as the recording medium. In addition, not only the computer program recorded on the recording medium that implements processing by itself, but also the computer program that operates on an OS to implement processing in cooperation with other software and/or expansion board functions is included in the scope of each embodiment.

<Supplementary Note>

With respect to the example embodiments described above, they may be further described as supplementary notes below, but are not limited to the following.

(Supplementary Note 1)

An information processing system of a supplementary note 1 is an information processing system comprising: a distance acquisition unit that specifies an iris area containing an iris of a target from a visible-light image of the target, and acquires an iris distance that is a distance to the iris area; an iris image acquisition unit that acquires an iris image of the target by changing a focal length according to the iris distance; a score computing unit that calculates a score relating to deviation of a focus in the iris image, based on the iris image; and a correlation update unit that updates correlation between the iris distance and the focal length at a moment of acquisition of the iris image, based on the score.

(Supplementary Note 2)

An information processing system of a supplementary note 2 is the information processing system according to the supplementary note 1, further comprising: a target information acquisition unit that acquires, with respect to the target, targe information that is information affects the iris distance which is acquired by the distance acquisition unit; and an iris distance correction unit that corrects the iris distance based on the target information, wherein the iris image acquisition unit changes the focal length by applying control voltage according to the iris distance.

(Supplementary Note 3)

An information processing system of a supplementary note 3 is the information processing system according to the supplementary note 1 or 2, further comprising: an environment information acquisition unit that acquires environment information relating to environment at a moment of acquisition of the iris image; and a correlation change unit that changes the correlation based on the environment information.

(Supplementary Note 4)

An information processing system of a supplementary note 4 is the information processing system according to any one of the supplementary notes 1 to 3, wherein the correlation update unit updates the correlation based on depth of field which is required for iris authentication using the iris image.

(Supplementary Note 5)

An information processing apparatus of a supplementary note 5 is an information processing apparatus comprising: a distance acquisition unit that specifies an iris area containing an iris of a target from a visible-light image of the target, and acquires an iris distance that is a distance to the iris area; an iris image acquisition unit that acquires an iris image of the target by changing a focal length according to the iris distance; a score computing unit that calculates a score relating to deviation of a focus in the iris image, based on the iris image; and a correlation update unit that updates correlation between the iris distance and the focal length at a moment of acquisition of the iris image, based on the score.

(Supplementary Note 6)

An information processing method of a supplementary note 6 is an information processing method to be implemented by at least one computer, comprising: specifying an iris area containing an iris of a target from a visible-light image of the target, and acquiring an iris distance that is a distance to the iris area; acquiring an iris image of the target by changing a focal length according to the iris distance; calculating a score relating to deviation of a focus in the iris image, based on the iris image; and updating correlation between the iris distance and the focal length at a moment of acquisition of the iris image, based on the score.

(Supplementary Note 7)

A recording medium of a supplementary note 7 is a recording medium storing a computer program that allows at least one computer to implement an information processing method, the information processing method comprising: specifying an iris area containing an iris of a target from a visible-light image of the target, and acquiring an iris distance that is a distance to the iris area; acquiring an iris image of the target by changing a focal length according to the iris distance; calculating a score relating to deviation of a focus in the iris image, based on the iris image; and updating correlation between the iris distance and the focal length at a moment of acquisition of the iris image, based on the score.

(Supplementary Note 8)

A computer program of a supplementary note 8 is a computer program that allows at least one computer to implement an information processing method, the information processing method comprising: specifying an iris area containing an iris of a target from a visible-light image of the target, and acquiring an iris distance that is a distance to the iris area; acquiring an iris image of the target by changing a focal length according to the iris distance; calculating a score relating to deviation of a focus in the iris image, based on the iris image; and updating correlation between the iris distance and the focal length at a moment of acquisition of the iris image, based on the score.

This disclosure is not limited to the above example embodiments. This disclosure can be modified as necessary to the extent that does not contradict the concept or idea of the invention which can be read from the entire claims and the entire description; and information processing systems, information processing apparatuses, information processing methods, and recording media with such changes are also included in the technical concept of this disclosure.

DESCRIPTION OF REFERENCE SIGNS

10 Information processing system
11 Processor
18 Camera
110 Iris distance acquisition unit
120 Iris image acquisition unit
121 Distance-voltage converting unit
122 Voltage applying unit
125 Focal length acquisition unit
126 Focal length control unit
130 Score computing unit
131 Image evaluation unit
140 Correlation update unit
141 Update determination unit
142 Depth-of-field setting unit
150 Target information acquisition unit
160 Iris distance correction unit
170 Environment information acquisition unit
180 Correlation change unit

The invention claimed is:

1. An information processing system comprising:
at least one memory storing instructions; and
at least one processor configured to execute the instructions to:
specify an iris area containing an iris of a target from a visible-light image of the target, and acquire an iris distance that is a distance to the iris area;
acquire an iris image of the target by changing a focal length according to the iris distance;
calculate a score relating to a deviation of a focus in the iris image, based on the iris image; and
update a correlation between the iris distance and the focal length at a time of acquisition of the iris image, based on a depth of field required for iris authentication using the iris image.

2. The information processing system according to claim 1, wherein
the at least one processor is further configured to execute the instructions to:
acquire, with respect to the target, target information that is information which affects the iris distance;
correct the iris distance based on the target information; and
change the focal length by applying a control voltage according to the iris distance.

3. The information processing system according to claim 1, wherein
the at least one processor is further configured to execute the instructions to:
acquire environment information relating to an environment at the time of acquisition of the iris image; and
change the correlation based on the environment information.

4. The information processing system according to claim 1, wherein
the at least one processor is further configured to execute the instructions to:
calculate scores by extracting feature amounts from a plurality of iris images taken consecutively and matching the feature amounts with each other with respect to anteroposterior images.

5. An information processing method to be implemented performed by at least one computer and comprising:
specifying an iris area containing an iris of a target from a visible-light image of the target, and acquiring an iris distance that is a distance to the iris area;
acquiring an iris image of the target by changing a focal length according to the iris distance;
calculating a score relating to a deviation of a focus in the iris image, based on the iris image; and
updating a correlation between the iris distance and the focal length at a time of acquisition of the iris image, based on a depth of field required for iris authentication using the iris image.

6. A non-transitory recording medium storing a computer program executable by at least one computer to perform an information processing method comprising:
specifying an iris area containing an iris of a target from a visible-light image of the target, and acquiring an iris distance that is a distance to the iris area;
acquiring an iris image of the target by changing a focal length according to the iris distance;
calculating a score relating to a deviation of a focus in the iris image, based on the iris image; and
updating a correlation between the iris distance and the focal length at a time of acquisition of the iris image, based on a depth of field required for iris authentication using the iris image.

* * * * *